US010888435B2

(12) United States Patent
Adamo et al.

(10) Patent No.: US 10,888,435 B2
(45) Date of Patent: Jan. 12, 2021

(54) MODULAR INSERTER FOR ANTERIOR CERVICAL CAGE

(71) Applicant: SPINE WAVE, INC., Shelton, CT (US)

(72) Inventors: Benoit Adamo, South Salem, NY (US);
David Boisvert, Southington, CT (US);
Scott McLean, Sandy Hook, CT (US);
David Considine, Milford, CT (US);
Andrew Bernhardt, Florence, SC (US)

(73) Assignee: SPINE WAVE, INC., Shelton, CT (US)

( * ) Notice: Subject to any disclaimer, the term of this patent is extended or adjusted under 35 U.S.C. 154(b) by 16 days.

(21) Appl. No.: 16/150,344

(22) Filed: Oct. 3, 2018

(65) Prior Publication Data
US 2019/0105180 A1   Apr. 11, 2019

Related U.S. Application Data

(60) Provisional application No. 62/568,575, filed on Oct. 5, 2017, provisional application No. 62/570,179, filed on Oct. 10, 2017.

(51) Int. Cl.
*A61F 2/46*   (2006.01)
*A61F 2/44*   (2006.01)
*A61F 2/30*   (2006.01)

(52) U.S. Cl.
CPC ............ *A61F 2/4603* (2013.01); *A61F 2/447* (2013.01); *A61F 2/4611* (2013.01);
(Continued)

(58) Field of Classification Search
CPC .............. A61F 17/1659; A61F 17/1662; A61F 17/1671; A61F 2/4603; A61F 2/4611;
(Continued)

(56) References Cited

U.S. PATENT DOCUMENTS 2,998,007 A   8/1961   Herzog
3,574,381 A   4/1971   Ocheltree et al.
(Continued)

FOREIGN PATENT DOCUMENTS

EP   0 064 724 A2   11/1982
FR   2827156 A1   1/2003

OTHER PUBLICATIONS

International Search Report for PCT/US2018/054092, dated Dec. 31, 2018.
Written Opinion for PCT/US2018/054092, dated Dec. 31, 2018.

*Primary Examiner* — Amy R Sipp
(74) *Attorney, Agent, or Firm* — Hoffmann & Baron, LLP

(57) ABSTRACT

A modular inserter assembly for use in inserting an interbody fusion cage into the disc space between opposing vertebrae comprises a depth stop and a modular inserter tip releasably attached thereto. The modular inserter assembly includes a cage attachment surface for releasable attachment to an interbody fusion cage, the depth stop including a movable stop axially movable relative to the inserter tip and being sized and configured to engage an exterior surface of one of the vertebrae to establish the depth to which the interbody fusion cage is to be inserted in the disc space. A plurality of modular inserter tips, each being configured for selective releasable attachment to differently sized interbody fusion cages are provided in a kit with the depth stop.

37 Claims, 18 Drawing Sheets

(52) U.S. Cl.
CPC .......... *A61F 2/4684* (2013.01); *A61F 2/4455* (2013.01); *A61F 2002/30507* (2013.01); *A61F 2002/30537* (2013.01); *A61F 2002/30616* (2013.01); *A61F 2002/4625* (2013.01); *A61F 2220/0025* (2013.01); *A61F 2230/0069* (2013.01)

(58) Field of Classification Search
CPC ...... A61F 2002/4625; A61F 2002/4627; A61F 2002/4628
See application file for complete search history.

(56) References Cited

U.S. PATENT DOCUMENTS

| | | | |
|---|---|---|---|
| 3,814,089 A | 6/1974 | Deyerle | |
| 4,275,717 A | 6/1981 | Bolesky | |
| 4,519,100 A | 5/1985 | Wills et al. | |
| 4,667,664 A | 5/1987 | Taylor et al. | |
| 4,848,327 A | 7/1989 | Perdue | |
| 4,892,545 A | 1/1990 | Day et al. | |
| 5,057,103 A | 10/1991 | Davis | |
| 5,397,364 A | 3/1995 | Kozak et al. | |
| 5,522,899 A | 6/1996 | Michelson | |
| 5,534,004 A | 7/1996 | Santangelo | |
| 5,601,550 A | 2/1997 | Esser | |
| 5,782,830 A | 7/1998 | Farris | |
| 5,800,550 A | 9/1998 | Sertich | |
| 5,810,820 A | 9/1998 | Santori et al. | |
| 5,971,986 A | 10/1999 | Santori et al. | |
| 5,976,139 A | 11/1999 | Bramlet | |
| 6,030,401 A | 2/2000 | Marino | |
| 6,077,264 A | 6/2000 | Chemello | |
| 6,099,531 A | 8/2000 | Bonutti | |
| 6,120,503 A | 9/2000 | Michelson | |
| 6,174,311 B1 | 1/2001 | Branch et al. | |
| 6,179,873 B1 | 1/2001 | Zientek | |
| 6,183,474 B1 | 2/2001 | Bramlet et al. | |
| 6,235,059 B1 | 5/2001 | Benezech et al. | |
| 6,342,057 B1 | 1/2002 | Brace et al. | |
| 6,342,074 B1 | 1/2002 | Simpson | |
| 6,379,364 B1 | 4/2002 | Brace et al. | |
| 6,409,768 B1 | 6/2002 | Tepic et al. | |
| 6,443,954 B1 | 9/2002 | Bramlet et al. | |
| 6,447,546 B1 | 9/2002 | Bramlet et al. | |
| 6,468,311 B2 | 10/2002 | Boyd et al. | |
| 6,527,803 B1 | 3/2003 | Crozet et al. | |
| 6,558,388 B1 | 5/2003 | Bartsch et al. | |
| 6,558,423 B1 | 5/2003 | Michelson | |
| 6,648,889 B2 | 11/2003 | Bramlet et al. | |
| 6,770,096 B2 | 8/2004 | Bolger et al. | |
| 7,056,344 B2 | 6/2006 | Ruppert et al. | |
| 7,223,289 B2 | 5/2007 | Trieu et al. | |
| 7,232,464 B2 | 6/2007 | Mathieu et al. | |
| 7,235,082 B2 | 6/2007 | Bartish et al. | |
| 7,416,553 B2 | 8/2008 | Patel et al. | |
| 7,594,931 B2 | 9/2009 | Louis et al. | |
| 7,674,287 B2 | 3/2010 | Alferness et al. | |
| 7,695,516 B2 | 4/2010 | Zeegers | |
| 7,776,047 B2 | 8/2010 | Fanger et al. | |
| 7,842,088 B2 | 11/2010 | Rashbaum et al. | |
| 7,846,207 B2 | 12/2010 | Lechmann et al. | |
| 7,909,829 B2 | 3/2011 | Patel et al. | |
| 7,909,848 B2 | 3/2011 | Patel et al. | |
| 7,935,123 B2 | 5/2011 | Fanger et al. | |
| 7,988,693 B2 | 8/2011 | Martz et al. | |
| 8,002,776 B2 | 8/2011 | Liu et al. | |
| 8,062,303 B2 | 11/2011 | Berry et al. | |
| 8,080,062 B2 | 12/2011 | Armstrong et al. | |
| 8,147,556 B2 | 4/2012 | Louis et al. | |
| 8,216,313 B2 | 7/2012 | Moore | |
| 8,257,439 B2 | 9/2012 | Zeegers | |
| 8,267,997 B2 | 9/2012 | Colleran | |
| 8,268,000 B2 | 9/2012 | Waugh et al. | |
| 8,273,127 B2 | 9/2012 | Jones et al. | |
| 8,282,682 B2 | 10/2012 | Kirschman | |
| 8,292,958 B1 | 10/2012 | Bruffey et al. | |
| 8,313,528 B1 | 11/2012 | Wensel | |
| 8,328,870 B2 | 12/2012 | Patel et al. | |
| 8,328,872 B2 | 12/2012 | Duffield et al. | |
| 8,343,219 B2 | 1/2013 | Allain et al. | |
| 8,377,133 B2 | 2/2013 | Yuan et al. | |
| 8,394,107 B2 | 3/2013 | Fanger et al. | |
| 8,409,285 B2 | 4/2013 | Keller | |
| 8,454,700 B2 | 6/2013 | Lemoine et al. | |
| 8,460,388 B2 | 6/2013 | Kirwan et al. | |
| 8,523,946 B1 | 9/2013 | Swann | |
| 8,617,245 B2 | 12/2013 | Brett | |
| 8,641,766 B2 | 2/2014 | Donner et al. | |
| 8,685,104 B2 | 4/2014 | Lee et al. | |
| 8,709,083 B2 | 4/2014 | Duffield et al. | |
| 8,728,165 B2 | 5/2014 | Parry et al. | |
| 8,840,651 B2 | 9/2014 | Reiley | |
| 8,864,830 B2 | 10/2014 | Malandain | |
| 8,906,101 B2 | 12/2014 | Lee et al. | |
| 8,932,359 B2 | 1/2015 | Brett | |
| 8,968,405 B2 | 3/2015 | Kirwan et al. | |
| 9,033,993 B2 | 5/2015 | Bae et al. | |
| 9,039,774 B2 | 5/2015 | Chataigner et al. | |
| 9,044,337 B2 | 6/2015 | Dinville et al. | |
| 9,078,765 B2 | 7/2015 | Louis et al. | |
| 9,101,489 B2 | 8/2015 | Protopsaltis et al. | |
| 9,155,631 B2 | 10/2015 | Seifert et al. | |
| 9,161,841 B2 | 10/2015 | Kana et al. | |
| 9,216,024 B2 | 12/2015 | Geisert et al. | |
| 9,241,809 B2 | 1/2016 | McDonough et al. | |
| 9,358,134 B2 | 6/2016 | Malandain | |
| 9,402,740 B1 | 8/2016 | Donaldson | |
| 9,402,741 B1 | 8/2016 | Donaldson | |
| 9,572,685 B2 | 2/2017 | Perry | |
| 9,937,055 B1 | 4/2018 | Bernhardt, Jr. et al. | |
| 2001/0011191 A1 | 8/2001 | Kohrs | |
| 2004/0082955 A1 | 4/2004 | Zirkle, Jr. | |
| 2007/0239616 A1 | 10/2007 | Kuenzi et al. | |
| 2007/0250167 A1 | 10/2007 | Bray et al. | |
| 2008/0243131 A1* | 10/2008 | Sorrenti | A61F 2/4611 606/99 |
| 2008/0249569 A1 | 10/2008 | Waugh et al. | |
| 2008/0281425 A1 | 11/2008 | Thalgott et al. | |
| 2009/0099601 A1 | 4/2009 | Aferzon et al. | |
| 2009/0164020 A1 | 6/2009 | Janowski et al. | |
| 2010/0016968 A1 | 1/2010 | Moore | |
| 2010/0145459 A1 | 6/2010 | McDonough et al. | |
| 2010/0185289 A1 | 7/2010 | Kirwan et al. | |
| 2011/0098747 A1 | 4/2011 | Donner et al. | |
| 2011/0208311 A1 | 8/2011 | Janowski | |
| 2012/0078373 A1 | 3/2012 | Gamache et al. | |
| 2012/0116466 A1 | 5/2012 | Dinville et al. | |
| 2012/0191166 A1 | 7/2012 | Louis et al. | |
| 2012/0197263 A1* | 8/2012 | Copf | A61F 2/446 606/104 |
| 2012/0197401 A1 | 8/2012 | Duncan et al. | |
| 2012/0253406 A1 | 10/2012 | Bae et al. | |
| 2012/0277872 A1 | 11/2012 | Kana et al. | |
| 2012/0277873 A1 | 11/2012 | Kana et al. | |
| 2013/0110242 A1 | 5/2013 | Kirwan et al. | |
| 2013/0150968 A1 | 6/2013 | Dinville et al. | |
| 2013/0226300 A1 | 8/2013 | Chataigner et al. | |
| 2013/0245767 A1 | 9/2013 | Lee et al. | |
| 2014/0088711 A1 | 3/2014 | Chin et al. | |
| 2014/0114413 A1 | 4/2014 | Allain et al. | |
| 2014/0142619 A1 | 5/2014 | Serina et al. | |
| 2014/0156010 A1 | 6/2014 | Lee et al. | |
| 2014/0163684 A1 | 6/2014 | Donner et al. | |
| 2014/0277456 A1 | 9/2014 | Kirschman | |
| 2014/0277477 A1 | 9/2014 | Malandain | |
| 2015/0051702 A1 | 2/2015 | Chataigner et al. | |
| 2015/0051704 A1 | 2/2015 | Duffield et al. | |
| 2015/0057754 A1 | 2/2015 | Reed et al. | |
| 2015/0127107 A1 | 5/2015 | Kim et al. | |
| 2015/0127109 A1 | 5/2015 | Brett | |
| 2015/0202051 A1* | 7/2015 | Tanaka | A61F 2/4657 623/17.16 |
| 2015/0209089 A1 | 7/2015 | Chataigner et al. | |

(56) References Cited

U.S. PATENT DOCUMENTS

| | | |
|---|---|---|
| 2015/0305883 A1 | 10/2015 | Garber et al. |
| 2015/0305887 A1 | 10/2015 | McAtamney et al. |
| 2016/0015523 A1 | 1/2016 | Lewis et al. |
| 2016/0151168 A1 | 6/2016 | Morris et al. |
| 2017/0112631 A1 | 4/2017 | Kuyler |

* cited by examiner

MODULAR INSERTER FOR ANTERIOR CERVICAL CAGE

CROSS-REFERENCE TO RELATED APPLICATION

This application claims the benefit of U.S. Provisional Patent Application No. 62/570,179, filed Oct. 10, 2017, the entire contents of which are incorporated by reference herein. This application also claims the benefit of U.S. Provisional Patent Application No. 62/568,575, filed Oct. 5, 2017, the entire contents of which are incorporated by reference herein.

FIELD OF THE INVENTION

The subject invention relates generally to the field of spinal instrumentation and more particularly to a modular spinal implant inserter assembly for use in inserting a spinal fusion cage between a superior vertebra and an inferior vertebra, the modular inserter assembly including a releasable depth stop and a releasable modular tip for attachment to the spinal fusion cage.

BACKGROUND OF THE INVENTION

Spinal implants such as interbody fusion devices are used to treat degenerative disc disease and other damages or defects in the spinal disc between adjacent vertebrae. The disc may be herniated or suffering from a variety of degenerative conditions, such that the anatomical function of the spinal disc is disrupted. Most prevalent surgical treatment for these conditions is to fuse the two vertebrae surrounding the affected disc. In most cases, the entire disc will be removed, except for a portion of the annulus, by way of a discectomy procedure. A spinal fusion device is then introduced into the intradiscal space and suitable bone graft or bone substitute material is placed substantially in and/or adjacent the device in order to promote fusion between two adjacent vertebrae.

One embodiment of a spinal device for cervical fusion is described in U.S. Patent Publication No. 2015/0202051, entitled "Spinal Fusion System", filed on Jan. 16, 2015 by Shigeru Tanaka et al. (the '051 Application) and assigned to the same assignee as the subject application. The entire contents of the '051 Application are incorporated herein by reference. The spinal fusion system described in the '051 Application includes an interbody fusion cage, a fixation plate with deployable anchor blades, and an implanter. In a particular arrangement described in the '051 Application, the system may further include a trial/sizer tool including a set of trial/sizer instruments. Such instruments may incorporate a pre-scoring blade to break the vertebral endplate prior to insertion of the spinal implant into the disc space and deployment of the blades into the endplates. As such, the trial device may serve two purposes, namely to test a size for a potential interbody fusion cage implant and to prepare one or more vertebral endplate surfaces for receiving the implant. The implanter includes a distal end configured for releasable coupling with the proximal end region of the interbody fusion cage. The implanter further includes a ramp distally projecting from the distal end of the implanter. The blades abut against sloped surfaces of the ramp, where the abutting causes the blades to divert from the non-deployed state to the deployed state.

Another example of a scoring trial and inserter assembly particularly useful in cervical fusion is shown and described in U.S. patent application Ser. No. 15/454,287, entitled "Scoring Implant Trial and Implant Inserter for Spinal Fusion System", filed on Mar. 9, 2017 by Andrew Bernhardt, Jr. et al. (the '287 Application) and assigned to the same assignee as the subject application. The entire contents of the '287 Application are incorporated herein by reference. The modular inserter assembly is used to introduce an interbody fusion cage with an anchor plate into the disc space between opposing vertebral bodies to an appropriate depth so that blades on the anchor plate will be deployed into the slots created in the endplates by the scoring element of the scoring trial. The adjustable depth stop of the modular inserter assembly includes readable values that correspond to the depth settings on the scoring trial. Intended use requires that the depth setting on the modular inserter assembly matches the depth setting on the scoring trial in order to position the fusion cage at the appropriate depth. With a pull rod, the modular inserter assembly also provides a mechanism to deploy the anchor plate.

While the implanter and inserter assembly of the respective '051 and '287 Applications are beneficial in spinal surgical procedures, a separate cage insertion instrument is typically required to be provided for each cage that may be used during a particular surgery. As such, the need for a plurality of inserter assemblies tends to lead to increased costs of surgery.

SUMMARY OF THE INVENTION

It is an object of the subject invention is to provide a more compact, lower cost fusion cage inserter assembly that employs modular inserter tips. A further object is to provide a kit comprising a plurality of modular inserter tips that are individually releasably attachable to a depth stop for a more compact, lower cost instrument offering.

DESCRIPTION OF THE EMBODIMENTS

Figure 1:
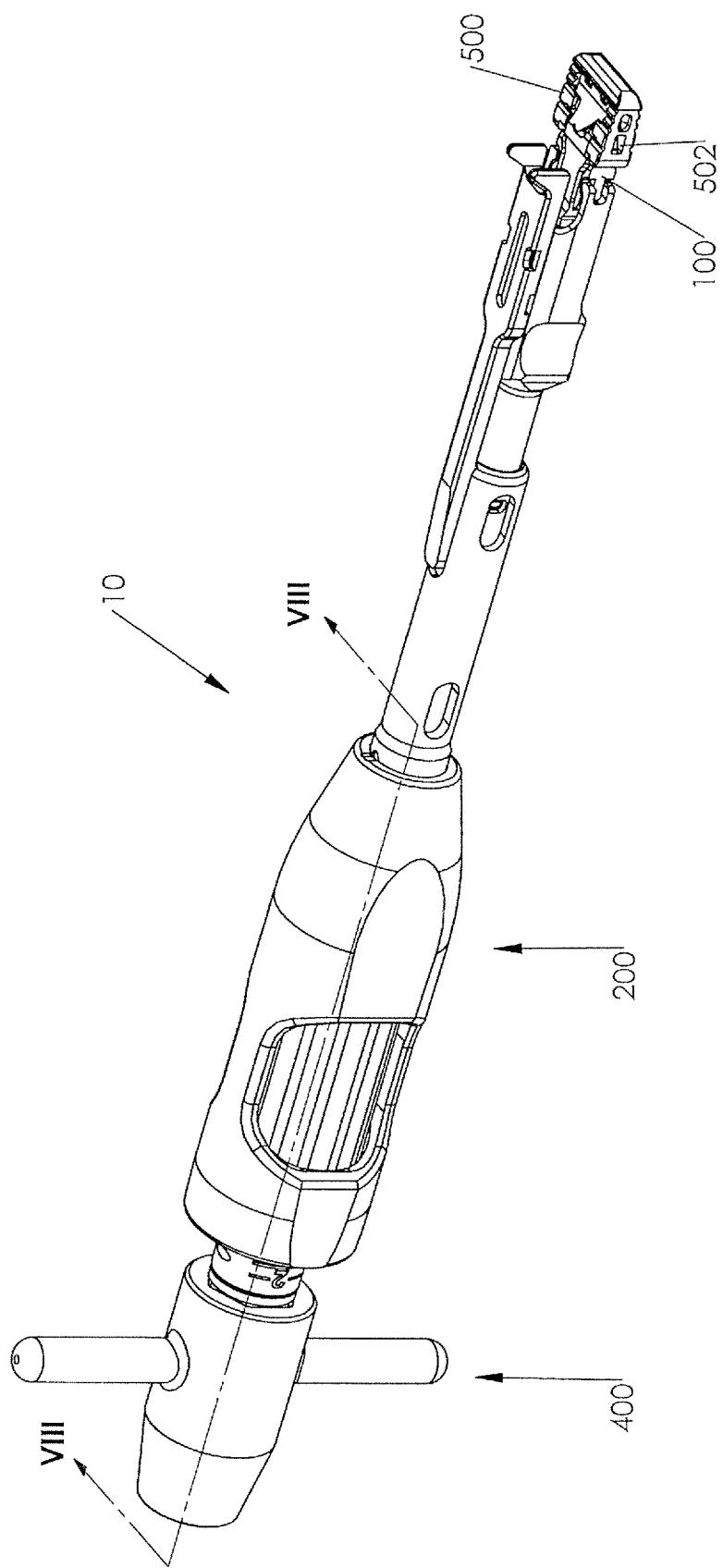
FIG. 1 is a top perspective view of a modular inserter assembly, in accordance with one embodiment of the present invention, for use in inserting an interbody fusion cage between opposing vertebra of a spine.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 2:
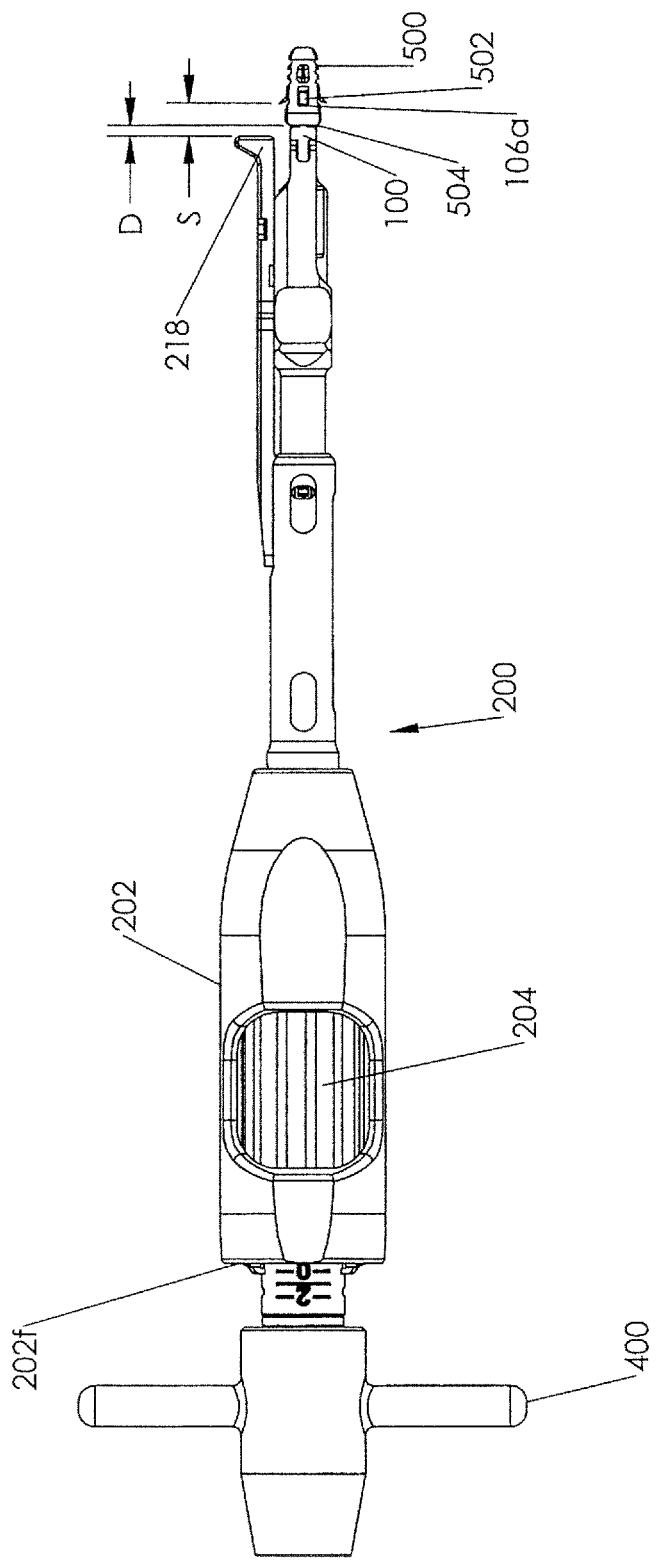
FIG. 2 is a side elevation view of the modular inserter assembly of FIG. 1.
Figure 3:
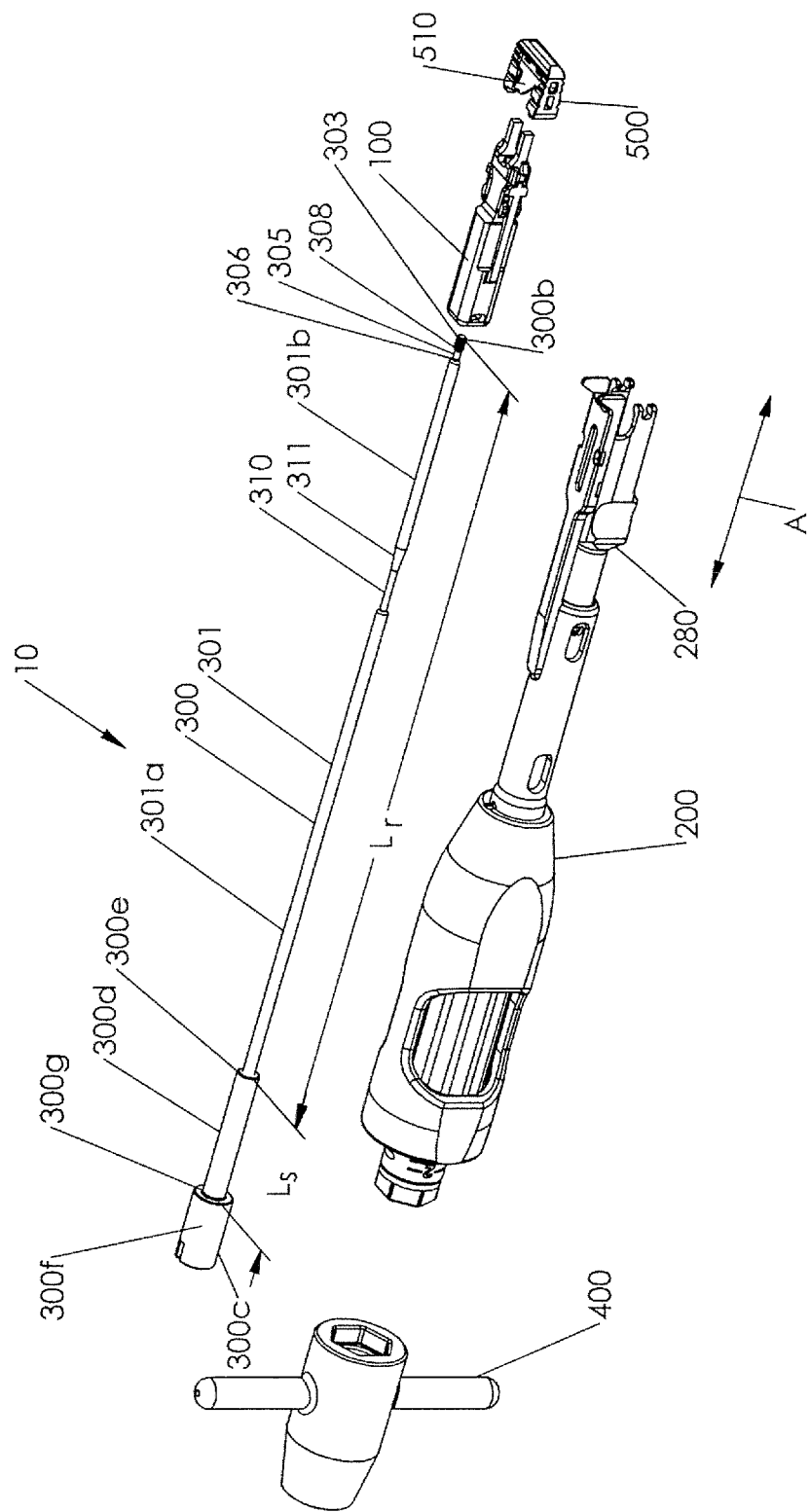
FIG. 3 is a top perspective exploded view of the modular inserter assembly of FIG. 1.

The present invention contemplates a modular inserter assembly 10 as depicted in FIGS. 1-3 for use in fusing together opposing superior and inferior vertebra of a spine. Modular inserter assembly 10 comprises a modular inserter tip 100, a depth stop 200 that is releasably attached to modular inserter tip 100, an elongate pull rod 300 movably axially supported by depth stop 200, and an actuator 400 shown in a particular form as a T-handle. Modular inserter assembly 10 is used to insert an interbody fusion device such as an anterior cervical cage 500 into a disc space between opposing vertebral bodies of a spine to the measured depth and to deploy blades of an anchor plate 510 movably supported by cage 500. Such an anterior cervical cage is described, for example, in the '287 Application, commonly assigned herewith. Depth stop 200 replicates the anterior-posterior depth determined by a disc preparation instrument so that the blades of anchor plate 500 will be deployed into the vertebral bodies at an appropriate location. A disc preparation instrument suitable for use in conjunction with inserter assembly 10 is described in U.S. application Ser. No. 16/150,335, entitled "Modular Scoring Trial for Anterior Cervical Cage", filed on even date herewith by Benoit Adamo, et al. (the '335 Application), assigned to the same assignee as the subject invention, and incorporated by reference herein in its entirety.

Figure 4:
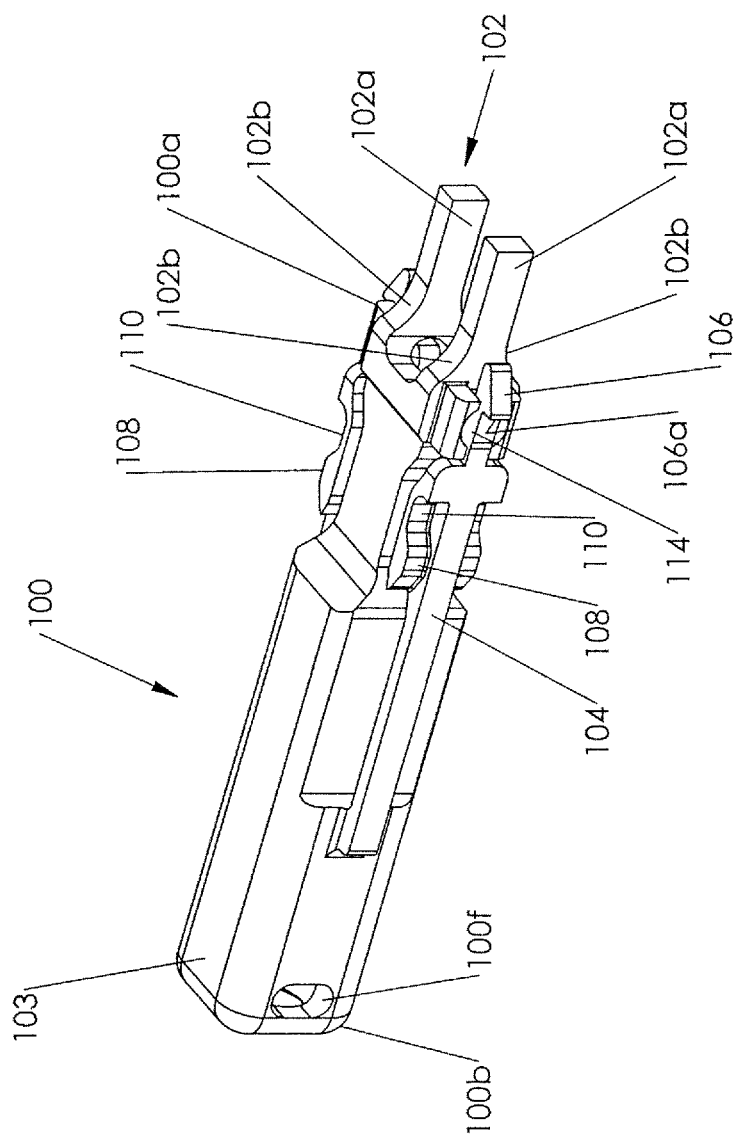
FIG. 4 is a top perspective view of the distal end of the modular inserter tip of the modular inserter assembly of FIG. 1.
Figures 5, 6:
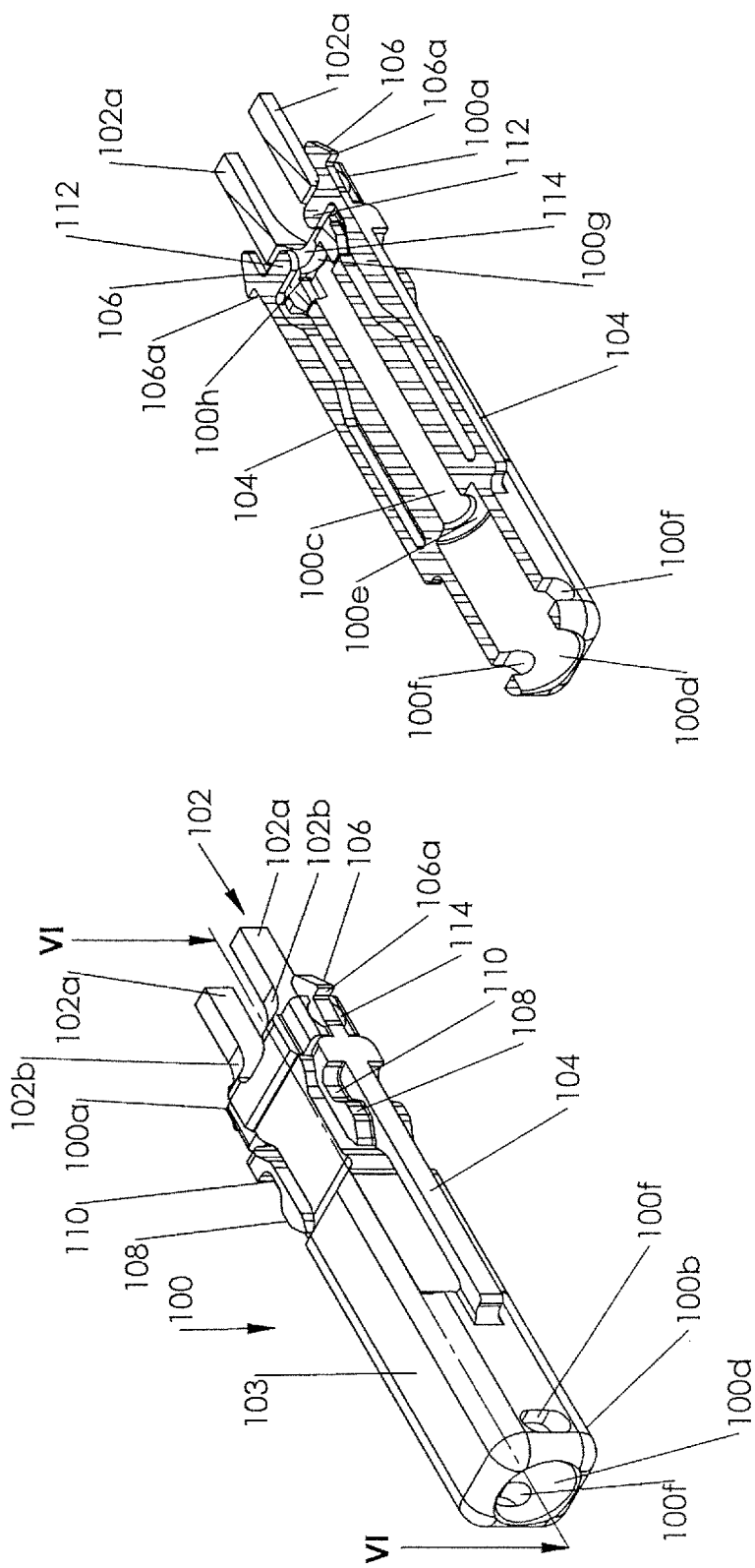
FIG. 5 is a top perspective view of the proximal end of the modular inserter tip of the modular inserter assembly of FIG. 1.
FIG. 6 is a longitudinal cross section of the modular inserter tip as seen along viewing lines VI-VI of FIG. 5

Turning now also to FIGS. 4, 5 and 6, the details of modular inserter tip 100 are described. Modular inserter tip 100 is of generally parallelepiped configuration having a distal end 100a and a proximal end 100b with a central bore 100c extending therethrough. Proximal end 100b of modular inserter tip 100 includes an exterior surface 103 having a generally square cross-section. Proximal end 100b includes a counterbore 100d extending therein for receipt of a portion of depth stop 200, as will be described. Counterbore 100d communicates with central bore 100c and terminates in an interior surface 100e extending transversely within modular inserter tip 100 and defining a depth stop contact surface. Proximal end 100b includes a pair of slots 100f on opposite sides of modular inserter tip 100 that together define a depth stop attachment surface.

Distal end 100a includes an anchor deployment ramp 102 projecting distally outwardly therefrom. Anchor deployment ramp 102 is sized and configured to extend into interbody fusion cage 500 and to direct blades of anchor plate 510 in substantially opposite directions. In a particular arrangement, anchor deployment ramp 102 comprises a pair of laterally spaced ramps 102a, each of which comprises opposite curvate surfaces 102b to facilitate the substantially opposite movement of anchor blades thereon as anchor plate 510 is drawn proximately along anchor deployment ramp 102, as will be described. Distal end 100a includes a pull rod opening 100g extending therethrough for receipt of an attachment end of pull rod 300, as will be described. Opening 100g communicates with central bore 100c and has a diameter slightly less than the diameter of central bore 100c such that an interior surface 100h extends transversely between central bore 100c and pull rod opening 100g.

Distal end 100a comprises a pair of bilateral flexible latches 104 terminating in outwardly directed hooks 106 for releasable attachment to interbody fusion cage 500. Each of hooks 106 includes a proximally facing surface 106a that together define a cage attachment surface. Hooks 106 are sized and configured to be received in slots 502 formed through opposing lateral walls of interbody fusion cage 500 such that cage attachment surface 106a engages a distally facing surface defining such slot 502, as shown in FIG. 1. Each of flexible latches 104 is supported in a particular arrangement as a cantilever with hooks 106 at the free unsupported end being movable toward and away from each other. Each flexible latch 104 further includes a cam 108 that facilitates release of modular inserter tip 100 from interbody fusion cage 500, as will be described. Located on each flexible latch 104 between cam 108 and hook 106 is a cavity 110 for releasable engagement with a portion of the proximal end of depth stop 200. Each flexible latch 104 also includes at its free unsupported end an inwardly directed post 112 slidingly received in a cross-bore 114 extending transversely through distal end 100a of modular inserter tip 100. Cross-bore 114 is formed to communicate with pull rod opening 100g. The transverse distance between opposing posts 112 is slightly greater than the outer diameter of center shaft distal portion 301b (FIGS. 3 and 12) of pull rod 300. As will be described, posts 112 assist in the locking of modular inserter tip 100 to interbody fusion cage 500 and facilitate the release of cage 500 from modular inserter tip 100 in conjunction with the proximal movement of pull rod 300.

Figure 7:
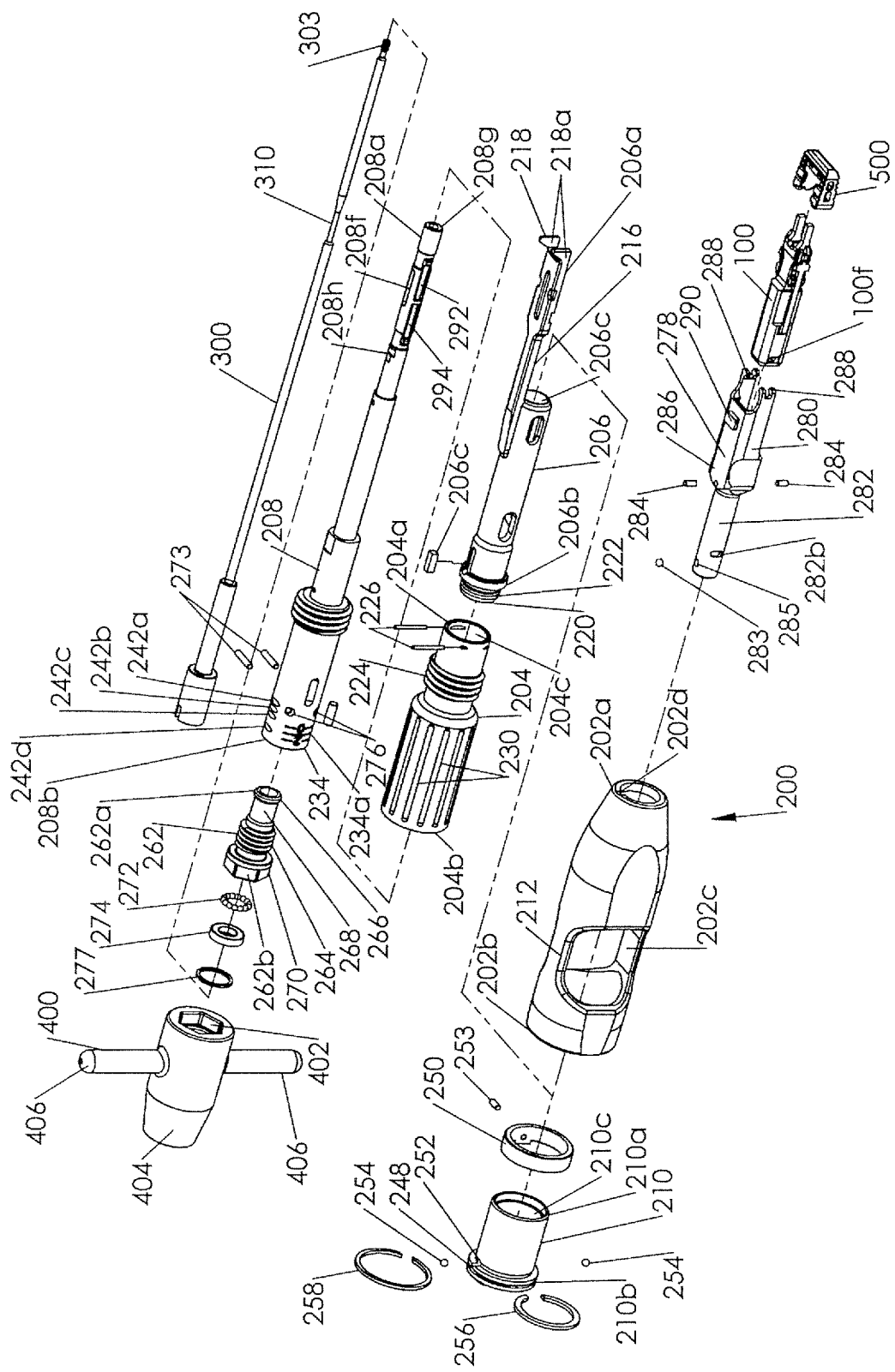
FIG. 7 is a top perspective exploded view of FIG. 1 showing components of the depth stop of the modular inserter assembly.
Figure 8:
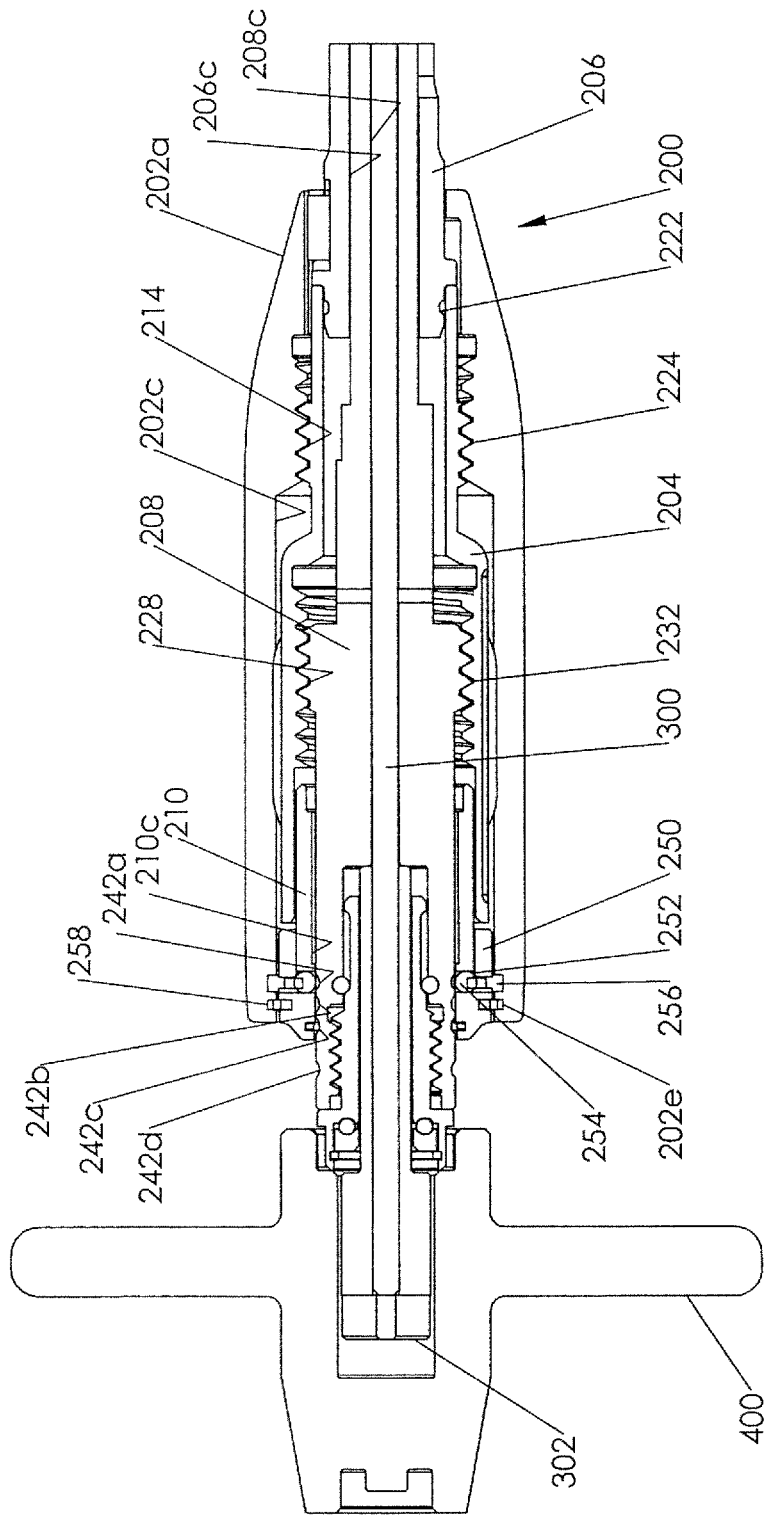
FIG. 8 is an enlarged sectional view of the proximal portion of the modular inserter assembly as seen along viewing lines VIII-VIII of FIG. 1 prior to deployment of anchor blades supported in the interbody fusion device.

Turning now also to FIGS. 7 and 8, further details of the depth stop 200 are described, particularly the depth measurement features and depth indicator device. Depth stop 200 comprises a handle 202, an adjustment knob 204, an elongate sleeve 206, a center shaft 208 and a bushing 210. Handle 202 is generally cylindrical having a distal end 202a, a proximal end 202b, and an interior surface 202c within which adjustment knob 204 and center shaft 208 are disposed. Handle 202 includes a window 212 extending through an exterior surface to expose portions of adjustable knob 204. Interior surface 202c of handle 202 comprises internal threads 214 disposed adjacent distal end 202a, as illustrated in FIG. 8. Threads 214 have a first predetermined pitch, such as 2 mm, with threads 214 being oriented in a first direction as a left-handed thread.

Elongate sleeve 206 is generally cylindrical having a distal end 206a and a proximal end 206b. Sleeve 206 includes an elongate extension 216 projecting distally, extension 216 terminating in a stop 218 for measuring the depth interbody fusion cage 500 is to be inserted into an intervertebral disc space, as will be described. In a particular arrangement, stop 218 is defined by pair of opposed laterally spaced shoulders 218a having substantially flat interior surfaces. Sleeve 206 has a lumen 206c of size and configuration to receive a portion of center shaft 208 therethrough. Proximal end 206b of sleeve 206 includes an attachment portion 220 including a circumferential groove 222.

Adjustment knob 204 is of generally cylindrical configuration having a distal end 204a and a proximal end 204b. Adjustment knob 204 includes external threads 224 adjacent distal end 204a that are threadably coupled with handle internal threads 214 as shown in FIG. 8, threads 224 having the same first predetermined pitch and left-handed direction as handle internal threads 214 establishing a first threaded connection, as will be described. Proximal end 206b of sleeve 206 is coupled to distal end 204a of adjustment knob 204 by a set of pins 226 extending through sleeve 206 and into groove 222. Such coupling enables adjustment knob 204 and sleeve 206 to move axially jointly while allowing for rotational relative movement therebetween, movable stop 218 being affixed at the distal end 206a of sleeve 206. Sleeve 206 is fixed with respect to handle 202 by a key 206c that engages a keyway 202d at the distal end 202a of handle 202. Interior surface 204c has adjacent the proximal end 204b of adjustment knob 204 internal threads 228, as illustrated in FIG. 8. Threads 228 have a second predetermined pitch, such as 2 mm, with threads 228 being right-handed threads and thereby oriented in a second direction, opposite the first direction of internal threads 214 of handle 202. In a particular arrangement, the second predetermined pitch of threads 228 is equal to that of the first predetermined pith of threads 214. Adjustment knob 204 includes a plurality of axially extending circumferentially spaced splines 230 that are exposed through handle window 212, splines 230 facilitating the manual rotation of adjustment knob 204, as will be described.

Center shaft 208 is generally cylindrical having a distal end 208a, a proximal end 208b and a lumen 208c extending therethrough as shown in FIGS. 7 and 8. Center shaft 208 comprises external threads 232, threads 232 having the same second predetermined pitch and right-handed direction as internal threads 228 of adjustment knob 204 for engagement in a second threaded connection, as will be described. An indicator device 234 at the proximal end 208b of center shaft 208 comprises a plurality of markings 234a, such as numerical indicia and gradations. Center shaft 208 further includes adjacent proximal end 208b a series of detent grooves 242a, 242b and 242c formed diametrically apart on the outer surface of center shaft 208, detent grooves 242a, 242b and 242c being spaced at predetermined axial intervals to correspond with increments of depth stop measurements as denoted by markings 234a of indicator device 234. A fourth set of proximal-most detent grooves 242d is also provided to provide an indication of the release of depth stop 200 from interbody fusion cage 500 as will be described. Distal end 208a of center shaft 208 terminates in a tip contact surface 208g for contacting a respective depth stop contact surface 100e on each modular inserter tip 100.

Bushing 210 is generally cylindrical having a distal end 210a, a proximal end 210b and an interior surface 210c. Proximal end 210b of bushing 210 includes a flange 246 having a circumferentially extending groove 248. Bushing 210 has a pair of diametrically opposed openings 252 distally adjacent flange 246, each opening 252 being formed to house therein a ball bearing 254. Each ball bearing 254 is resiliently retained in a respective opening 252 by a spring member, such as a C-clip 256 that is captured between flange 246 and a collar 250. Collar 250 may be joined to bushing 210 by a pin 253 or otherwise secured thereto by any other suitable means, such as welding. C-clip 256 applies a radially inward bias force to ball bearings 254 in a manner that allows a circumferential portion of each ball bearing 254 to resiliently radially move inwardly and outwardly of interior surface 210c of bushing 210. As such, ball bearings 254 define a spring biased surmountable ball detent with grooves 242a-d on center shaft 208, as will be described. Further, the engagement of ball bearings 254 in respective detent grooves 242 provides tactile feedback and an audible click. A locking ring 258 is retained in groove 248 for connecting bushing 210 to interior surface 202c of handle 202 with locking ring 258 residing in interior groove 202e as shown in FIG. 8.

Referring back to FIG. 3, details of the elongate pull rod 300 are described. Pull rod 300 comprises an elongate central shaft 300a, a distal end 300b and a proximal end 300c. Central shaft 301 includes a proximal portion 301a and a distal portion 301b. The outer diameter of distal portion 301b may be less than or equal to the outer diameter of proximal portion 301a, as will be described. Toward proximal end 300b pull rod 300 includes a step portion 300d having a diameter greater than the outer diameter of central shaft proximal portion 301a. A transverse surface 300e is included on the distal face of step portion 300d and extends between the outer diameters of central shaft proximal portion 301a and step portion 300d, transverse surface 300e defining a force transmission surface as will be described. Central shaft 301 has a length, $L_R$ extending between transverse surface 300e and the distal end 300b of pull rod 300. Pull rod 300 terminates at the proximal end 300c in an enlarged head 300f having a diameter greater than the diameter of step portion 300d. A transverse surface 300g extends between the outer diameters of head 300f and step portion 300d at the distal face of head 300f, transverse surface 300g defining an engagement surface to facilitate proximal movement of pull rod 300, as will be described. Step portion 300d has a length, $L_S$ between transverse surfaces 300e and 300g. Lengths L$_R$ and L$_S$ and the outer diameters of central shaft proximal portion 301a and distal portion 301b may be formed in various dimensions to provide different pull rods 300 particularly suited for use with differently sized modular inserter tips 100 and interbody fusion cages 500, as will be described.

Pull rod 300 terminates at the distal end 300b in a threaded extent 303 for threaded engagement with anchor plate 510, as will be described. Proximally adjacent threaded extent 303, pull rod 300 includes an annular recess 305 having a diameter less than the diameter of central shaft distal portion 301b. Annular recess 305 is bounded on the proximal side by a shoulder 306 and on the distal side by a flange 308, more clearly seen in FIG. 12. The outer diameter of flange 308 is slightly greater than the maximum outer diameter of the threads of threaded extent 303, greater than the diameter of annular recess 305, and less than the outer diameter of central shaft distal portion 301b. Between central shaft proximal portion 301a and distal portion 301b, a radial relief 310 is formed. Radial relief 310 has a diameter less than the diameters of central shaft proximal portion 301a and distal portion 301b and includes a tapered portion 311 tapering up toward central shaft distal portion 301b.

Figure 9:
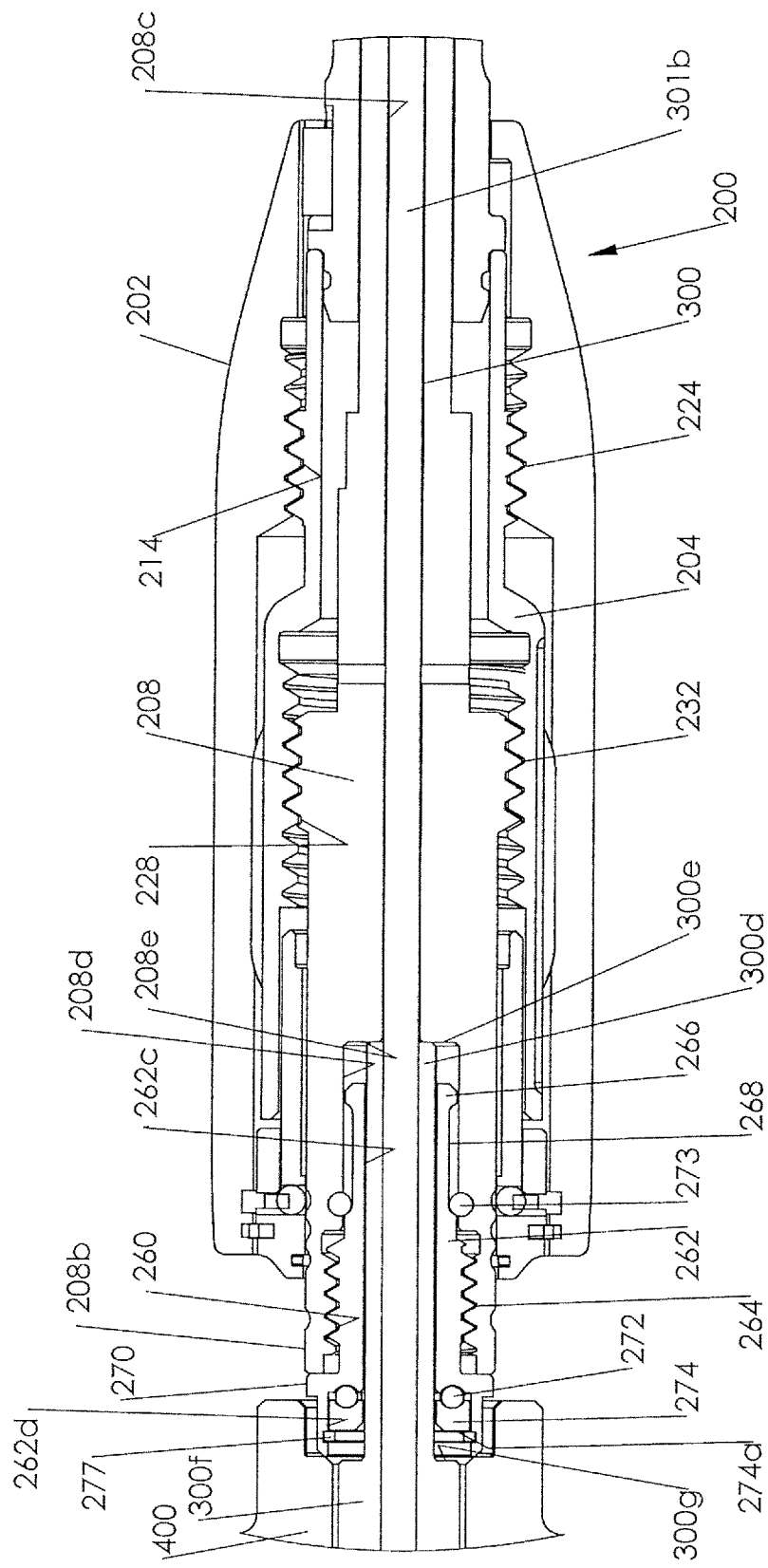
FIG. 9 is a further enlarged partial view of FIG. 8.

With further reference to FIGS. 3 and 7 and also now to FIG. 9, details of the pull rod movement feature of the depth stop 200 in conjunction with rod 300 are described. Center shaft 208 at its proximal end 208b includes a counterbore 208d communicating with center shaft lumen 208c. A transverse surface 208e extends between counterbore 208d and lumen 208c, transverse surface 208e defining an engagement surface to engage force transmission surface 300e of elongate pull rod 300 to transmit axial force to the interbody fusion cage 500 during insertion into the intervertebral space, as will be described. Internal threads 260 are formed at the proximal end of counterbore 208d.

A deployment screw 262 having a generally cylindrical configuration is provided. Deployment screw 262 has a distal end 262a, a proximal end 262b and a central opening 262c extending therethrough. Central opening 262c has a diameter sized and configured to receive step portion 300d elongate pull rod 300 therein. Between distal end 262a and proximal end 262b deployment screw 262 includes external threads 264 for threaded engagement with internal threads 260 of center shaft 208. Deployment screw 262 includes at its distal end 262a a radial flange 266 defining a radial recess 268 between flange 266 and external threads 264. Deployment screw 262 terminates at its proximal end 262b in an enlarged drive surface 270 for cooperative mating engagement with a drive socket 402 formed in T-handle 400 as shown in FIG. 7. Drive surface 270 in a particular configuration is hexagonal, although any suitable noncircular surfaces may be used. Deployment screw 262 is attached to center shaft 208 for rotational but limited axial movement by a pair of pins 273 extending into openings 276 through proximal portion 208b of center shaft 208. Pins 273 reside in radial recess 268 allowing deployment screw 262 to move axially only to the extent of the axial length of radial recess 268.

A counterbore 262d is formed in the proximal end 262b of deployment screw 262 in communication with central opening 262c. A ring of ball bearings 272 supported by a bearing race 274 is disposed within counterbore 262d. Ball bearings 272 and bearing race 274 are contained within counterbore 262d by a locking ring 277. Bearings 272 supported by bearing race 274 allow deployment screw 262 to rotate within center shaft 208 relative to elongate pull rod 300. Locking ring 277 has an inner diameter slightly greater than the outer diameter of pull rod head 300f, allowing head 300f to pass through locking ring 277 and engage proximal surface 274a of bearing race 274. The proximal surface 274a of bearing race 274 defines a contact surface for contacting engagement surface 300g of elongate pull rod 300 in a manner to axially move pull rod 300 in the proximal direction, as will be described. The diameter of elongate pull rod step portion 300d is sized and configured to extend through deployment screw central opening 262c in close sliding fit to allow transmission surface 300e of pull rod 300 to contact engagement surface 208e on center shaft 208, as will be described.

Figure 10:
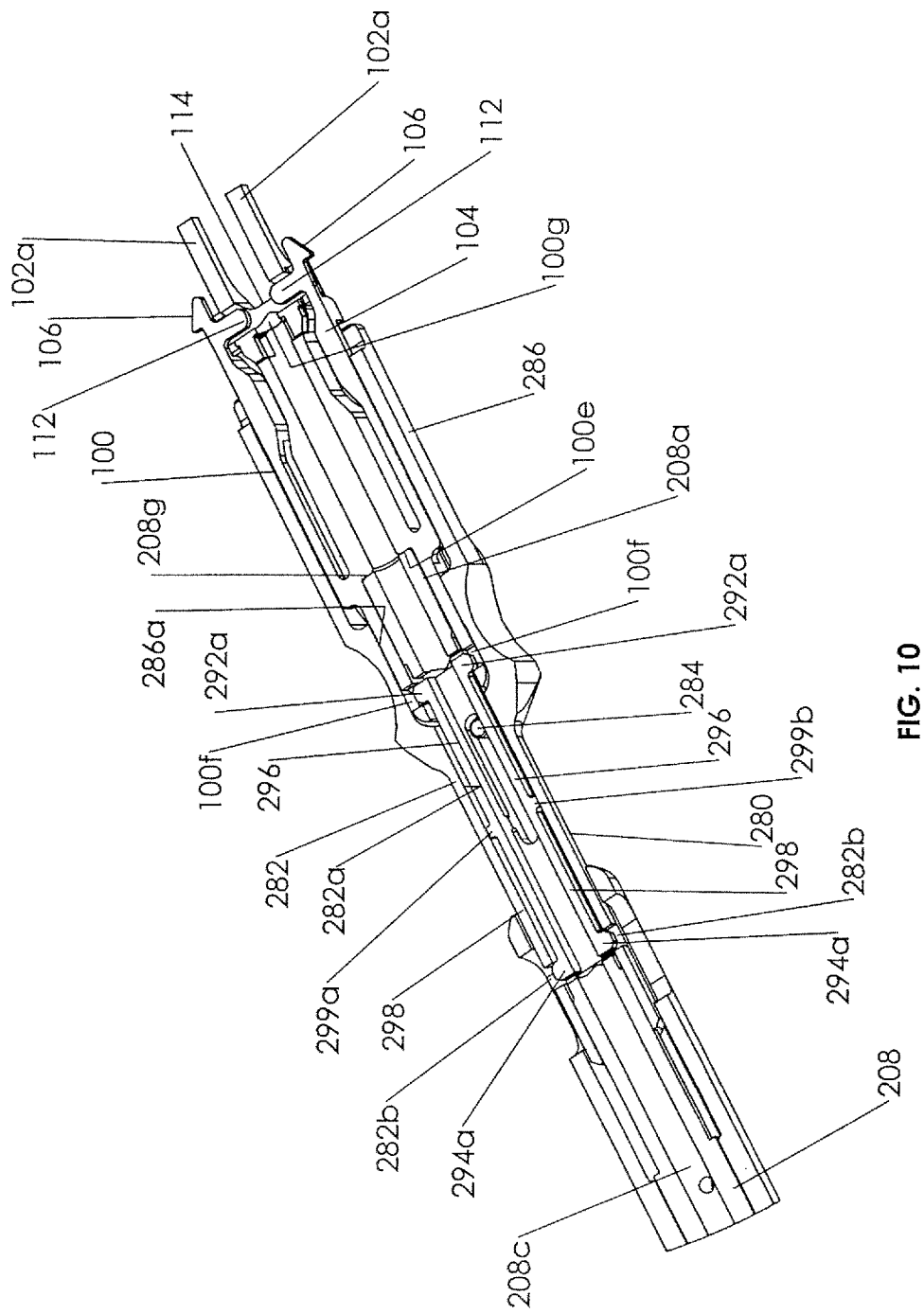
FIG. 10 is a longitudinal sectional view of the distal end of the depth stop of the modular inserter assembly of FIG. 1 with the modular inserter tip attached, but without the interbody fusion cage.
Figure 11:
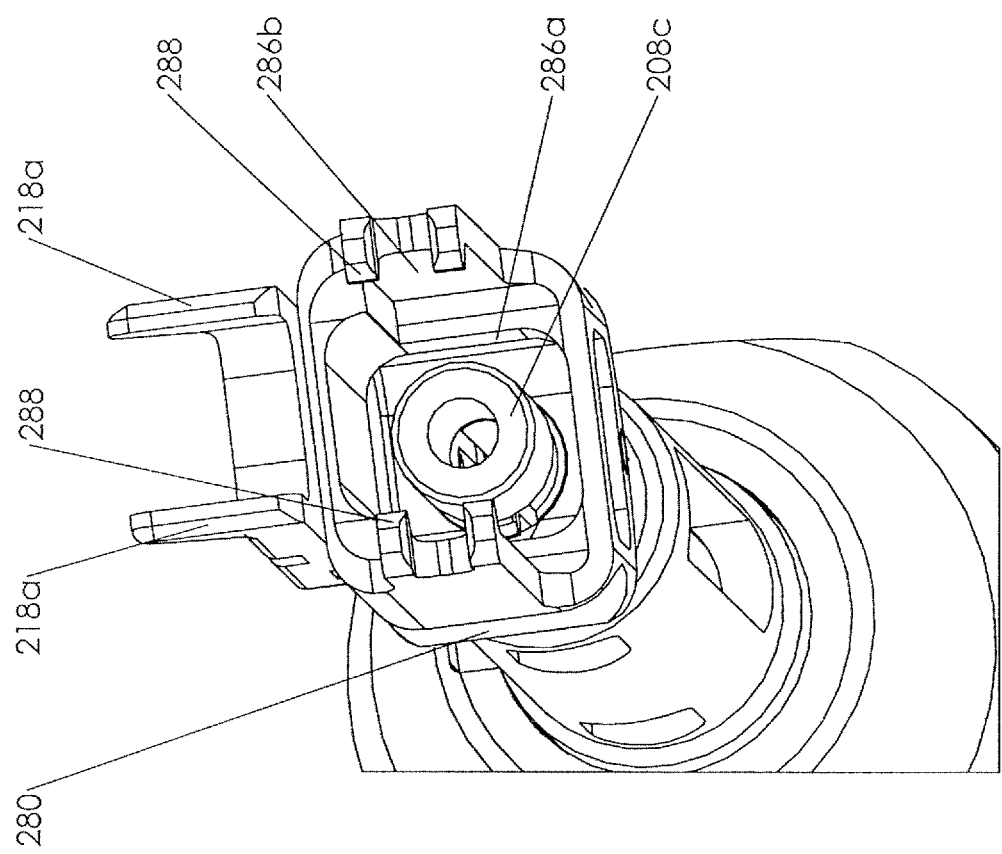
FIG. 11 is a perspective view of the modular inserter assembly as viewed distally to proximally prior to attachment to the modular inserter tip of FIG. 4.

With reference still to FIG. 7 and now also to FIGS. 10 and 11 details of locking features between depth stop 200 and modular inserter tip 100 are described. Movably attached to the distal end 208a of center shaft 208 is a movable locking element 278. In a particular arrangement, locking element 278 is a sliding cover 280 that is movable axially as shown by arrow, A in FIG. 3 from a first position to a second position, as will be described. The proximal end of sliding cover 280 comprises a tubular portion 282 having an interior opening 282a that receives and slides over distal end 208a of center shaft 208. A pair of slots 282b on opposite lateral sides of the tubular portion 282 together define a detent for surmountably holding sliding cover 280 in the first position, as will be described. Sliding cover 280 is slidably attached to distal end 208a of center shaft 208 by a pair of pins 284 that extend through a pair of opposing elongate slots 208f in center shaft 208. The extent of axial movement of sliding cover 280 on distal end 208a of center shaft 208 is determined by the axial length of elongate slot 208f. A ball bearing 283 is supported in a notch 208h formed in the exterior surface of center shaft 208 and captured in a cavity 285 formed through tubular portion 282, as shown in FIG. 7. As will be described, ball bearing 283 facilitates locking of sliding cover 280 relative to center shaft 208.

Distal end of sliding cover 280 comprises an elongate hollow body 286 having a generally rectangular exterior surface. Body 286 includes a first generally square internal pocket 286a and a second larger generally square internal pocket 286b. First internal pocket 286a is sized and configured to slidably mate with the generally square exterior surface of the proximal end 100b of modular inserter tip 100, while second internal pocket 286b interfaces with the exterior surfaces of latches 104 of modular inserter tip 100. Sliding cover 280 includes a pair of opposing bilateral tines 288 projecting from the distal end of sliding cover 280. Tines 288 are relatively rigid and respectively extend into cavities 110 of modular inserter tip 100 when sliding cover 280 is in the first position and participate in the separation of modular inserter tip 100 from the interbody fusion cage 500 during movement of cover 280 toward the second position, as will be described. A pad 290 formed on the top surface of sliding cover 282 projects toward sleeve extension 216.

Referring still to FIG. 10, features for releasably locking sliding cover 282 to center shaft 208 and modular inserter tip 100 are now described. Distal end 208a of center shaft includes a first pair 292 and a second pair 294 of bilateral flexible locking prongs 292a and 292b, each pair 292, 294 being axially spaced from each other. Prongs 292a and 294a are disposed at the free end of cantilever arms 296 and 298, each of which is respectively supported by a central support 299a and 299b therebetween. The first pair 292 of prongs of 292a is sized and arranged to be disposed in slots 100f of modular inserter tip 100 and the second pair 294 of prongs 294a is sized and arranged to be disposed in slots 282b of sliding cover 280. Interior surfaces of cantilever arms 296, 298 are linear and coincident with the inner surface of lumen 208c of center shaft 208 in a manner to allow elongate pull rod 300 to pass therethrough.

Having described the modular inserter assembly 10, the function and operation of indicator device 234 of inserter assembly 10 is now described with particular reference to FIGS. 7-8 and FIG. 2. Indicator device 234 is operable with the axial distal movement of handle 202 relative to center shaft 208 to provide a visual indication of a plurality of selectable distances that stop 218 may move relative to the proximal end 504 of interbody fusion cage 500. Clockwise rotation of adjustment knob 204 causes adjustment knob 204 via the second threaded connection between threads 228 and 232 to move adjustment knob 204 axially in a distal direction relative to center shaft 208 which is axially affixed to interbody fusion cage 500 via modular inserter tip 100. Additionally, such clockwise rotation of adjustment knob 204 via the first threaded connection between threads 214 and 224 causes handle 202 to also move axially distally relative to center shaft 208. Distal movement of adjustment knob 204 causes sleeve 206 and attached stop 218 to move distally relative to a first location on modular inserter tip 100 or interbody fusion cage 500. It should be understood that counterclockwise rotation of adjustment knob 204 will cause adjustment knob 204 and handle 202 to move proximally relative to center shaft 208 at the rates as described herein.

The first location may be cage attachment surface 106a of modular inserter tip 100 that is spaced from stop 218 by a distance, S, as shown in FIG. 2. In the alternative, first location may be the proximal end 504 of interbody fusion cage 500, as also shown in FIG. 2. The proximal surface of each of slots 502 that engages cage attachment surface 106a of modular inserter tip 100 is formed to be a predetermined distance from cage proximal end 504. As such, the first location on either modular tip 100 or interbody fusion cage 500 is correlatable. Each distance, D, for example, that stop 218 is selectively spaced from proximal end 504 of cage 500 is indicated by a different marking 234a that will be visually observable upon the axial distal movement of handle 202 which progressively exposes markings 234a at the proximal end 208b of center shaft 208 relative to a reference element on depth stop 200. Such reference element in one approach is defined by end surface 202f at the proximal end of handle 202, as depicted in FIG. 2. In a particular arrangement, markings 234a are two millimeters apart for ease of viewing but indicate one-millimeter increments of depth stop motion. This is accomplished via the two threaded connections (214/224 and 228/232) described above of the same pitch but opposing directions. As such, when the adjustment knob 204 is rotated, relative axial translation between the handle 202 and center shaft 208 with markings 234a thereon occurs at twice the rate of axial translation between stop 218 and proximal end 504. As a result, indicator device 234 provides an amplified indication of each of the selectively different distances, D between stop 218 and proximal end 504 of cage 500. Such amplified indication allows a surgeon to more readily appreciate the location at which fusion cage 500 may be placed in an intradiscal space, which is typically measured in millimeters and is relatively difficult to visually discern. It should be understood that while the threaded connections (214/224 and 228/232) are formed in opposing directions with each threaded connection having a pitch of 2 mm, similar differential rates of movement as described herein may be achieved with the threaded connections being in a common direction but of different pitches.

In this particular arrangement, indicator device 234 includes three indicia, denoted as "0", "1", and "2". The spacing in indicator device 234 between each of these markings is two millimeters, each of which represents a distance, D of 1 mm increment. The "0" marking may indicate a distance, D of approximately 2 mm, the "1" marking a distance, D of approximately 3 mm, and the "2" marking a distance, D of approximately 4 mm. As illustrated in FIG. 2, marking "0" is shown, indicating that stop 218 is measured at a distance, D of approximately 2 mm from proximal end 504 of interbody fusion cage 500. As handle 202 translates distally relative to center shaft 208, spring biased detent balls 254 sequentially engage detent grooves 242a, 242b or 242c that are spaced apart at predetermined axial intervals corresponding to markings 234a on indicator device 234, providing tactile feedback and an audible click to the surgeon as each interval is reached. In the example shown in FIG. 2 where the marking "0" is shown detent balls 254 would be engaged in grooves 242c, and in grooves 242a when the indicator device 234 reads "2".

A method of using modular inserter assembly 10 in an interbody fusion procedure is now described. While modular inserter assembly 10 may be used as a stand-alone instrument, it is particularly intended to be used in conjunction with the disc preparation instrument as shown and described in the commonly assigned '335 Application. Such an instrument is used to determine an appropriate size interbody fusion cage 500, the depth in the intradiscal space to which the cage 500 is to be inserted, and to score the endplates of opposing vertebral bodies at a desired location for receipt of deployable anchor blades supported by the cage 500. The disc preparation instrument of the '335 Application utilizes a depth stop having an indicator device that is substantially the same as indicator device 234 described herein. As such, when the size of the desired cage 500 and depth to which such cage 500 is to be inserted in disc space are determined by such a disc preparation instrument, the surgeon will note the readout of the indicator device on the disc preparation instrument. Such indicator readout will then be transferred to the indicator device 234 of the subject modular inserter assembly 10. In this regard, movable stop 218 would be selectively moved relative to center shaft 208 by rotation, of the adjustment knob 204 until a marking 234a matching the readout of the disc preparation instrument is indicated. For example, if the readout on the disc preparation instrument is "0", the surgeon would rotate adjustable knob 204 in either the clockwise or counterclockwise direction until indicator device 234 reads "0". This establishes the first distance, D that the stop will be spaced from a location on the interbody fusion cage, such as its proximal end 504. At that point, the surgeon would select the appropriate modular inserter tip 100 and interbody fusion cage 500 as determined by the modular scoring trial of the disc preparation instrument.

Figure 12:
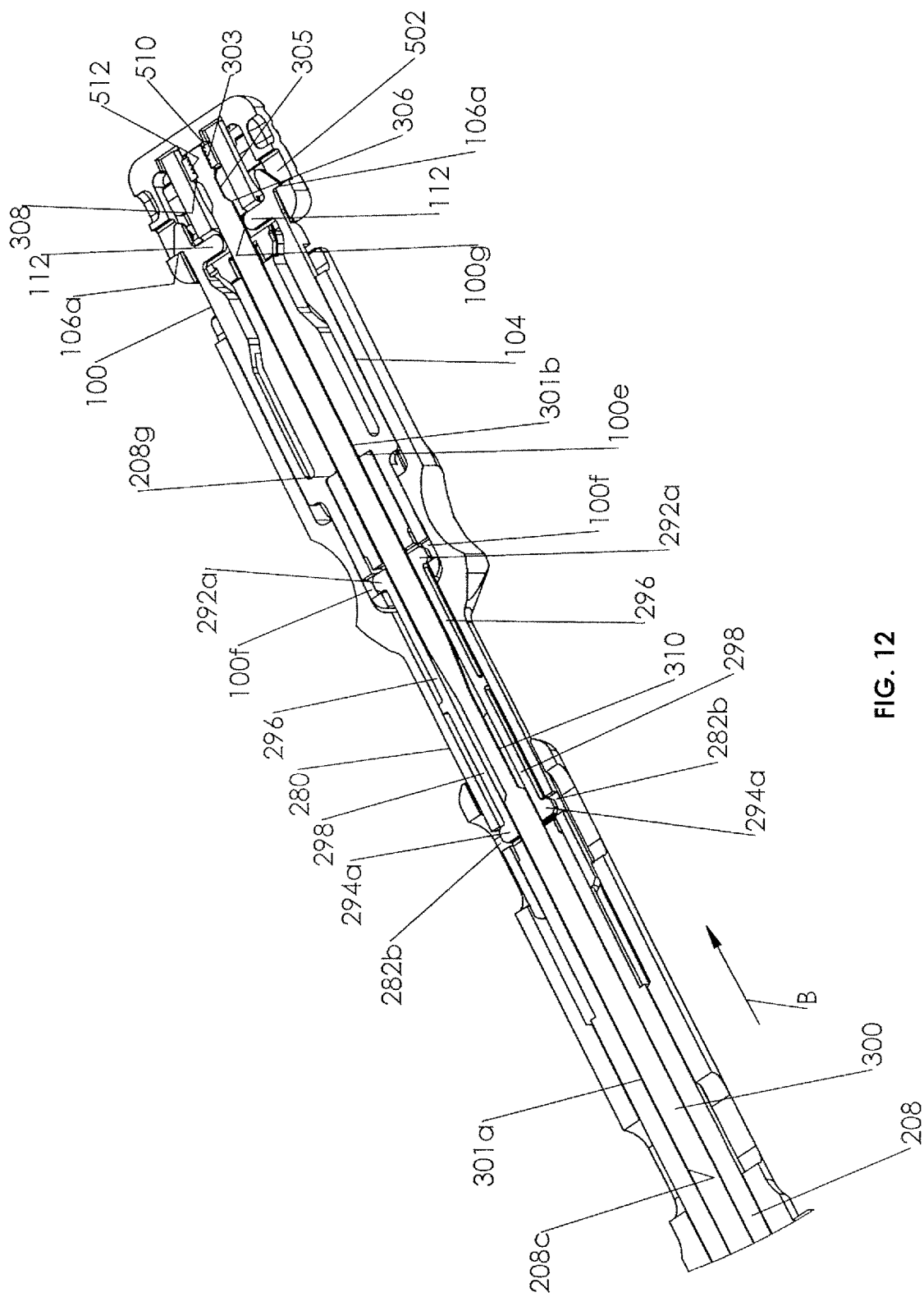
FIG. 12 is the sectional view of FIG. 10 showing the interbody fusion cage attached to the modular inserter tip and the elongate pull rod introduced through the depth stop and threadably attached to the anchor plate in the interbody fusion cage prior to deployment of anchor blades.

Once determined, the selected modular inserter tip 100 is then releasably attached to center shaft 208 until tip contact surface 208g contacts depth stop contact surface 100e on modular inserter tip 100 and flexible prongs 292a engage slots 100f of modular inserter tip 100. Then, the selected interbody fusion cage 500 is releasably attached to the selected modular inserter tip 100 by snapping the flexible latches 104 of modular inserter tip 100 into cage slots 502, as shown in FIG. 12. During such attachment, posts 112 on latches 104 move radially within cross-bore 114 inwardly toward each other, and after attachment snap back to the position shown in FIG. 10. Sliding cover 280 is then slid along center shaft 208 as shown by arrow B distally to the first position upon rotation of adjustment knob 204 and under the influence of ball bearing 283, as will be described, such that flexible prongs 294a engage slots 282b of sliding cover 280. An appropriately sized pull rod 300 is then selected and introduced from the proximal end of depth stop 200 and through lumen 208c of center shaft 208 until threaded extent 303 of pull rod 300 extends through opening 100g of modular inserter tip 100. With the appropriately sized pull rod 300, shoulder 306 and flange 308 on opposing ends of annular recess 305 will likewise extend through opening 100g of modular inserter tip 100. Pull rod 300 is rotated in a manner to threadably attach threaded extent 303 to threads 512 formed in anchor plate 510. Threading continues until flange 308 adjacent threaded extent 303 engages the outer proximal surface of anchor plate 510, thereby fully securing pull rod 300 to anchor plate 510. At this stage force transmission surface 300e is in contact with engagement surface 208e on center shaft 208, as shown in FIG. 9.

At this point, radial relief 310 on pull rod 300 is situated between flexible prongs 292a, 294a with exterior surface of central shaft 300a of pull rod 300 contacting interior surfaces of cantilevered arms 296 and 298. As such, prongs 292a and 294a are prevented from moving inwardly into a lumen 208c, thereby locking modular inserter tip 100 to sliding cover 280 and locking sliding cover 280 in the first position by preventing axial movement of sliding cover 280 relative to center shaft 208. Also, at this point, annular recess 305 of pull rod 300 has extended distally of modular inserter tip 100 and is situated within cage 500 with opposing posts 112 closely spaced to central shaft 300a of pull rod 300, as shown in FIG. 12. In this position opposing posts 112 are prevented from moving inwardly into cross-bore 114, thereby locking modular inserter tip 100 to cage 500.

Referring back now to FIGS. 8 and 9, the proximal end of the modular inserter assembly 10 is shown in the condition with elongate pull rod 300 attached to anchor plate 510 as shown in FIG. 12, with blades of anchor plate not deployed. In the example described herein wherein the surgeon has transferred the readout of "0" of the disc preparation instrument to the indicator device 234 of the subject modular inserter assembly 10, ball bearings 254 are in proximal most detent grooves 242c. Once pull rod 300 is fully tightened to anchor plate 510 force transmission surface 300e of pull rod 300, as described above, is in contact with engagement surface 208e on center shaft 208. As such, prior to the attachment of T-handle 400, inserter assembly 10 is used as an instrument to insert interbody fusion cage 500 attached thereto into the intradiscal space between vertebral bodies. In certain situations, the surgeon may use a tapping force to assist in the introduction of the cage into the intradiscal space. Suitable force may be applied to the proximal end 302 of the pull rod head 300f as shown in FIG. 8 to transmit an axial force to the interbody fusion cage 500 during insertion into the intervertebral space. Prior to deployment of the blades of anchor plate 510, contact surface 274a of bearing race 274 is spaced from transverse surface 300g that is provided to facilitate proximal movement of pull rod 300, as shown in FIG. 9.

Figure 13:
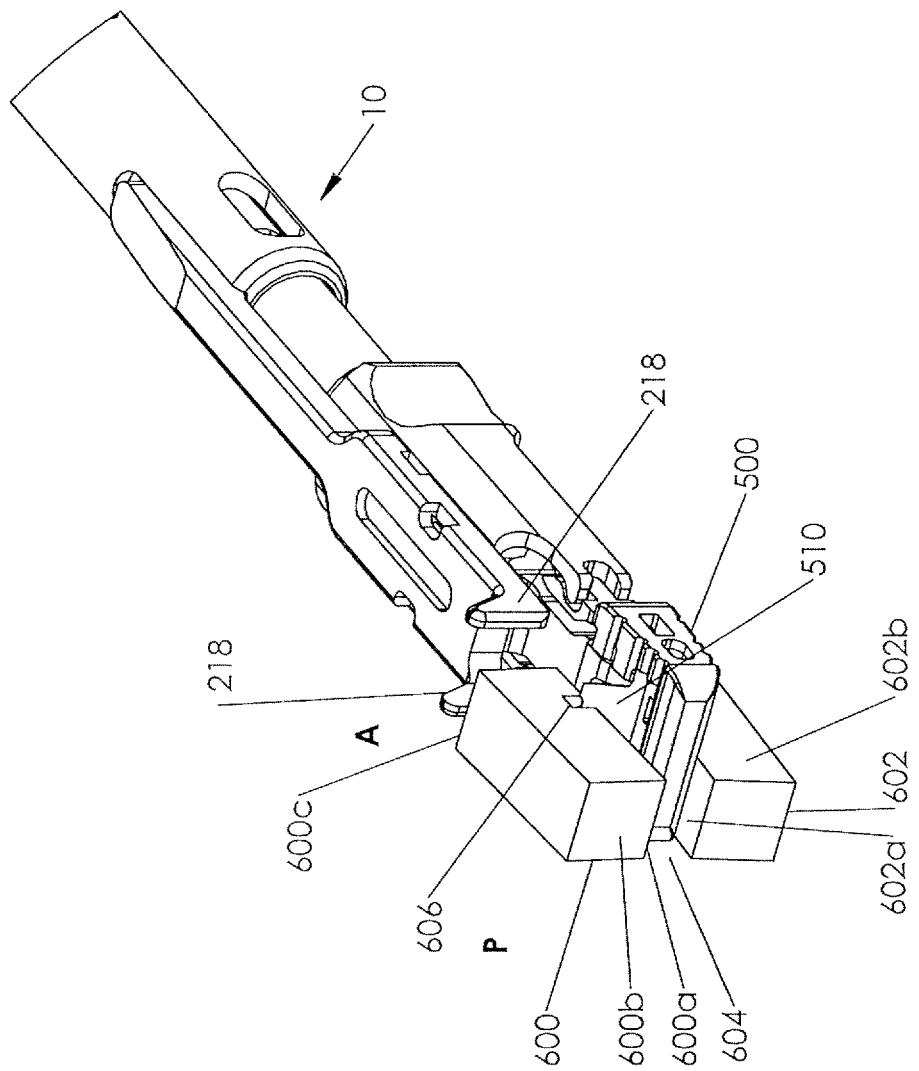
FIG. 13 is a perspective view showing the distal end of the modular inserter assembly with an interbody fusion cage being disposed in an intradiscal space between two opposing vertebral bodies of a spine prior to deployment blades, the vertebral bodies being partially sectioned for clarity.

FIG. 13 shows the use of modular inserter assembly 10 for the insertion of interbody fusion cage 500 into the cervical region of the spine in a procedure known as a Smith-Robinson approach. It should be appreciated, however, that inserter assembly 10 may also be used in interbody fusion procedures in other regions of the spine. It should be understood that access may be provided in other approaches, such as posterior or lateral in lumbar/thoracic procedures, as well as in other spinal surgeries, such as corpectomies.

Superior vertebra 600 includes an inferior endplate 600a, a vertebral body 600b, and an exterior anterior surface 600c. Inferior vertebra 602 includes a superior endplate 602a, a vertebral body 602b and an exterior anterior surface 602c (not seen). Superior endplate 600a and inferior endplate 602a define an intradiscal space 604 therebetween. Prior to insertion of interbody fusion cage 500 a suitable slot 606 has been scored into endplates 600a, 602a by an instrument such as the modular scoring trial of the '335 Application. With the desired depth of cage insertion having been set on depth stop indicator device 234, as transferred, for example, from the disc preparation instrument of the '335 Application, the insertion of cage 500 into disc space 604 continues until stops 218 contact exterior anterior surfaces 600c and 602c of the respective vertebral bodies 600 and 602. This establishes the desired depth to which cage 500 is inserted. Proper location of cage 500 may be confirmed by suitable imaging techniques, such as fluoroscopy. At this point, the penetration tips of deployable anchor blades of anchor plate 510 will be aligned with slots 606 and ready for deployment.

Figure 14:
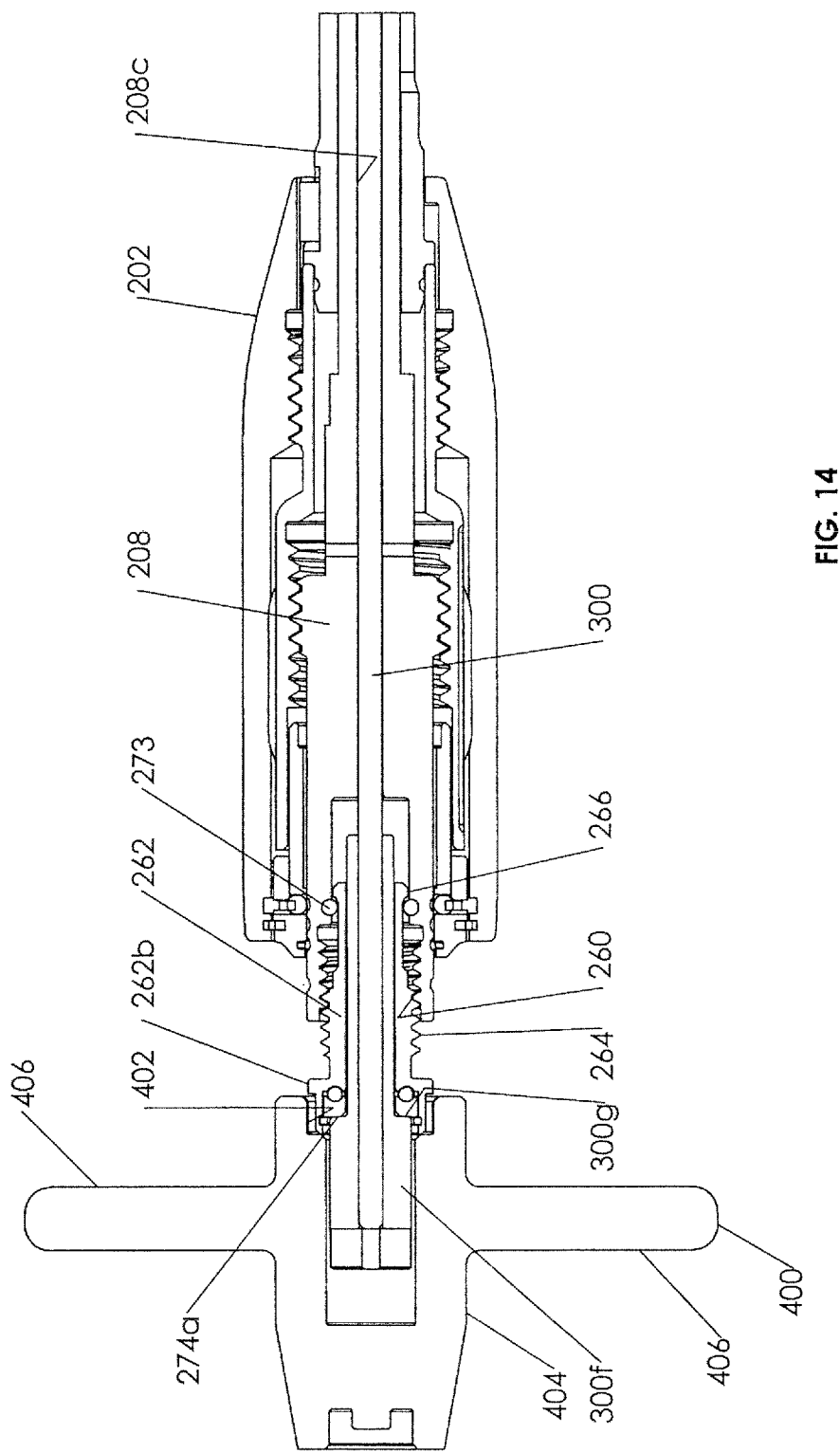
FIG. 14 is the sectional view of FIG. 8 after deployment of anchor blades supported in the interbody fusion device.

FIG. 14 shows the proximal portion of the modular inserter assembly 10 after the deployment of anchor blades supported in interbody fusion device 500. After insertion of interbody fusion cage 500 by inserter assembly 10 as described with respect to FIG. 13, actuator 400 may be attached to pull rod head 300f to effectuate anchor blade deployment. Actuator 400 comprises a generally cylindrical central hub 404 that includes drive socket 402 extending therein. Actuator 400 includes a pair of manually graspable extensions 406 projecting radially oppositely from central hub 404 and defining thereby a T-handle. Clockwise rotation of actuator 400 rotates deployment screw 262 causing deployment screw 262 to move axially proximally relative to center shaft 208 as a result of the threaded connection between threads 260/264, as described hereinabove. With pull rod 300 axially fixed relative to center shaft 208 as a result of the threaded connection to anchor plate 510, deployment screw 262 will continue to move proximally relative to pull rod 300 until contact surface 274a of bearing race 274 contacts transverse surface 300g of pull rod head 300f, as shown in FIG. 14. Continued clockwise rotation of T-handle 400 will draw pull rod 300 proximally relative to center shaft 208 until pins 273 engage flange 266 at the distal end of deployment screw 262.

Figure 15:
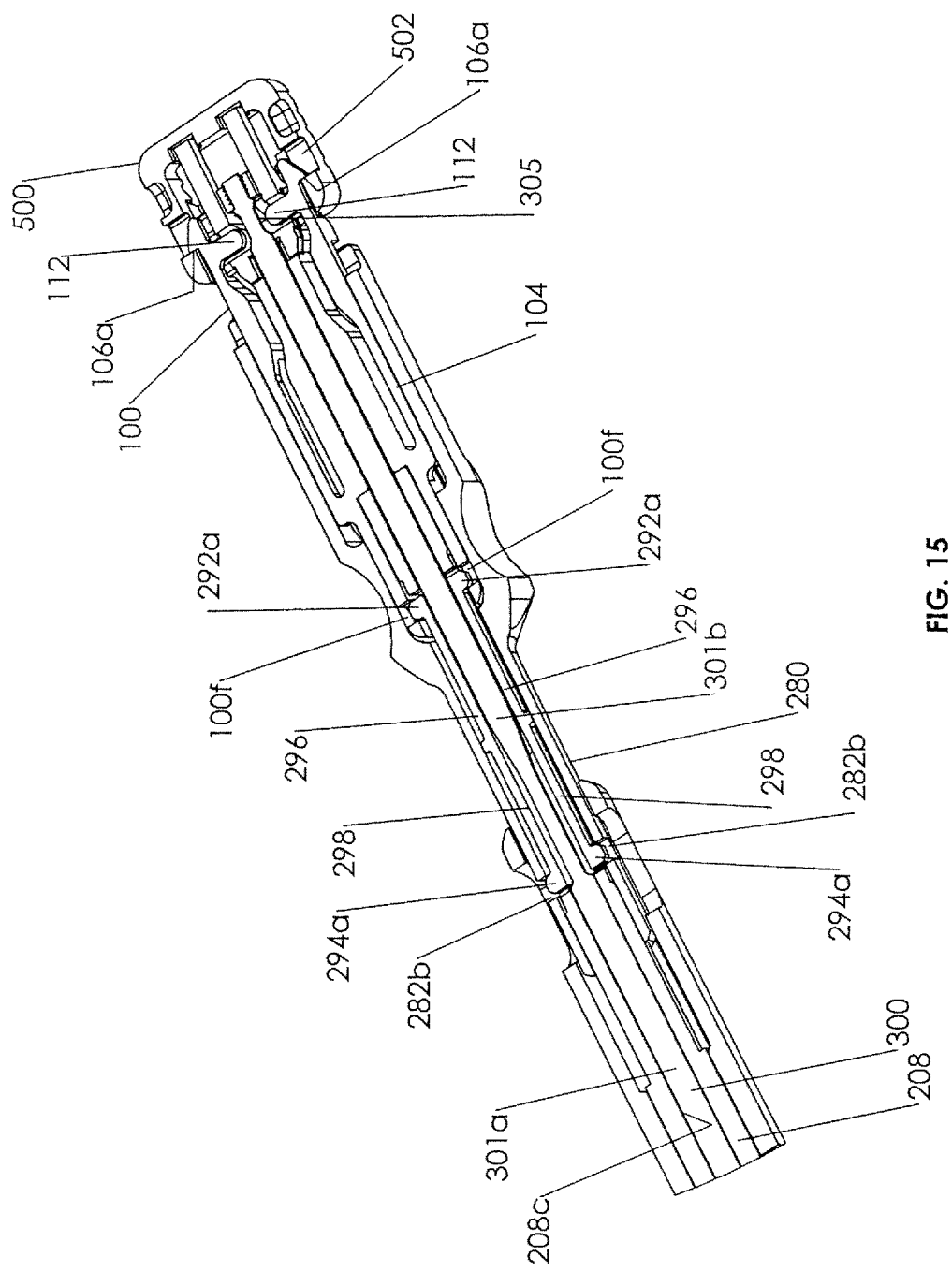
FIG. 15 is the sectional view of FIG. 12 showing the elongate pull rod moved proximally to deploy the anchor blades supported in the interbody fusion device.
Figure 16A:
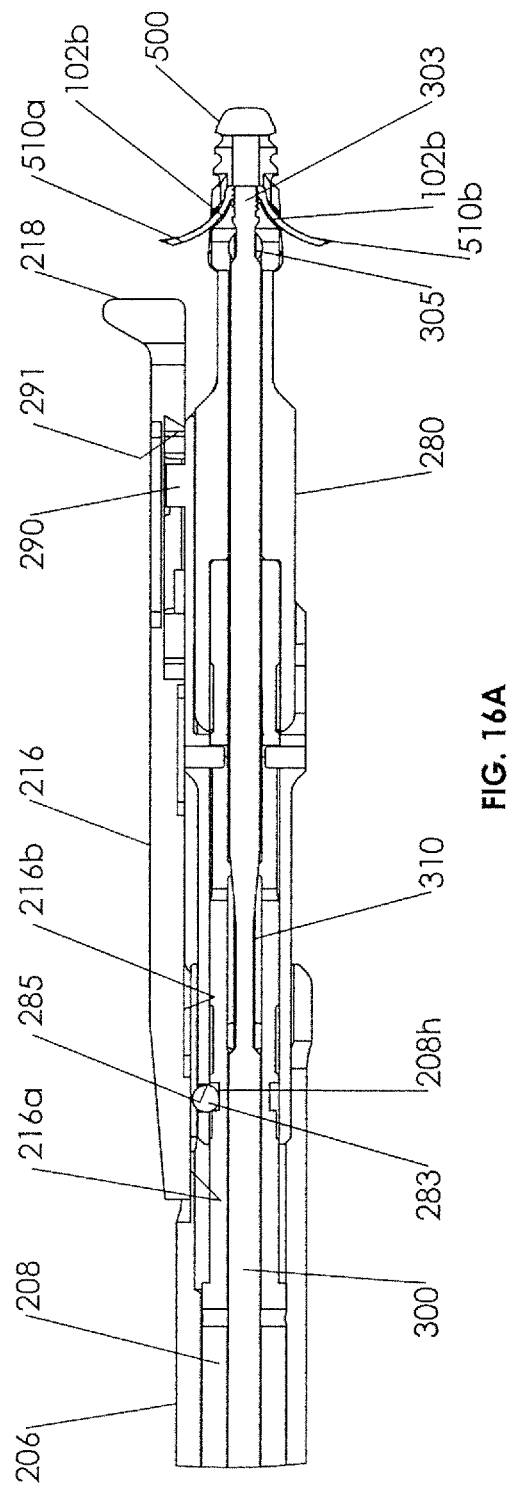
FIG. 16A is a longitudinal sectional view of the distal end of the modular inserter assembly of FIG. 2 showing anchor blades in a deployed position and the sliding cover in a first position relative to the inserter center shaft.
Figure 17:
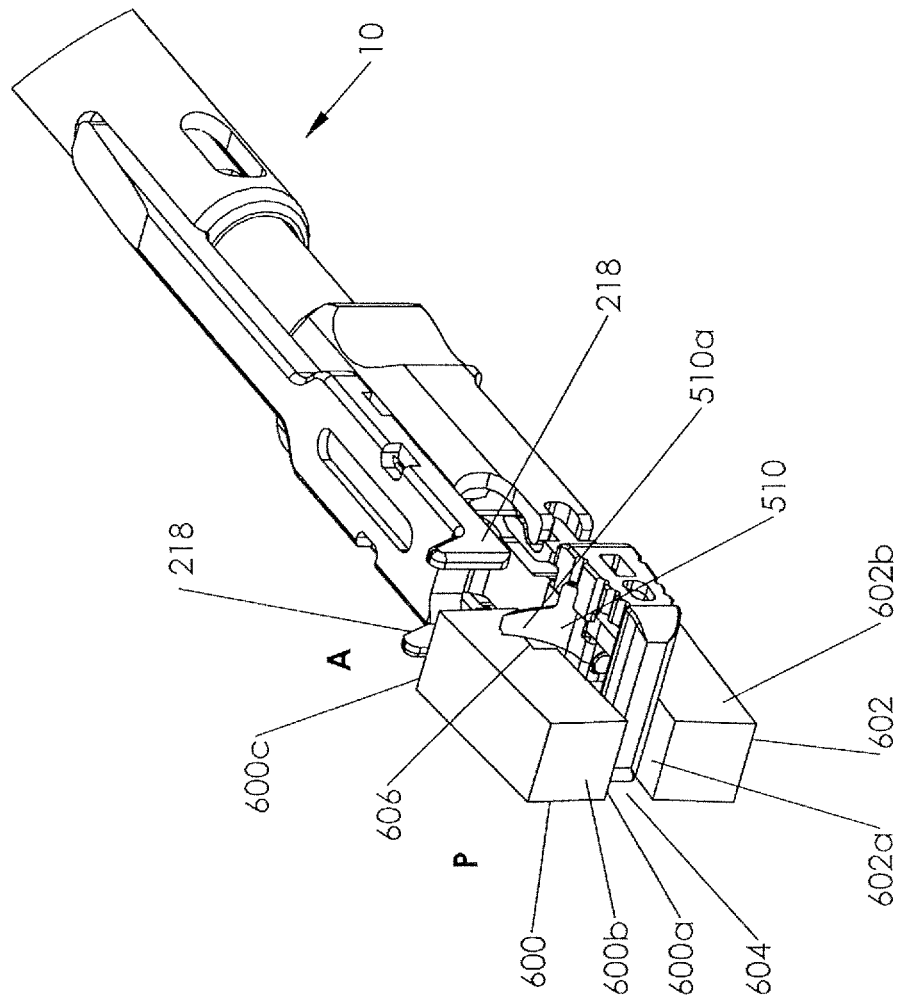
FIG. 17 is the perspective view of FIG. 13 after deployment of anchor blades supported in the interbody fusion device.

As pull rod 300 is moved axially proximally upon rotation of deployment screw 262 as described with respect to FIG. 14, pull rod distal end 300b moves proximally with respect to interbody fusion cage 500, as shown in FIG. 15. With the threaded extent 303 of pull rod 300 being threadably attached to anchor plate 510, upper anchor blade 510a and lower anchor blade 510b as illustrated in FIG. 16a slidably engage opposite curvate surfaces 102b of deployment anchor 102 to direct such blades 510a, 510b in substantially opposite directions. Such movement causes blades 510a, 510b to enter slots 606 that have been scored into opposing vertebral body endplates 600a, 602a of vertebral bodies, as illustrated in FIG. 17.

Referring again to FIG. 15, as pull rod 300 is translated in the proximal direction, pull rod radial relief 310 is moved to a position in alignment with second pair of prongs 294a. As such, there is no contact between cantilever arms 298 supporting prongs 294a and the pull rod 300. On the other hand, contact between exterior surface of pull rod distal portion 301 band cantilever arms 296 supporting first pair of prongs 292a is maintained. Accordingly, in this position, second pair of prongs 294a are in condition to be flexibly moved out from slots 282b of sliding cover 280 while first pair of prongs 292a remain in a locked position relative to modular inserter tip 100. While pull rod 300 remains attached to anchor plate 510, no sliding movement of modular tip relative to center shaft 208 can occur. In this position annular recess 305 has moved proximally with the proximal movement of pull rod 300 such that annular recess 305 is in axial alignment with opposing posts 112 on modular inserter tip 100. Accordingly, posts 112 are in condition to be flexibly moved radially inwardly within cross-bore 114 and toward annular recess 305 so as to allow hooks 106 on modular inserter tip 100 to flexibly move out from slots 502 on interbody fusion cage 500 to thereby separate cage 500 from modular inserter tip 100.

Figure 16B:
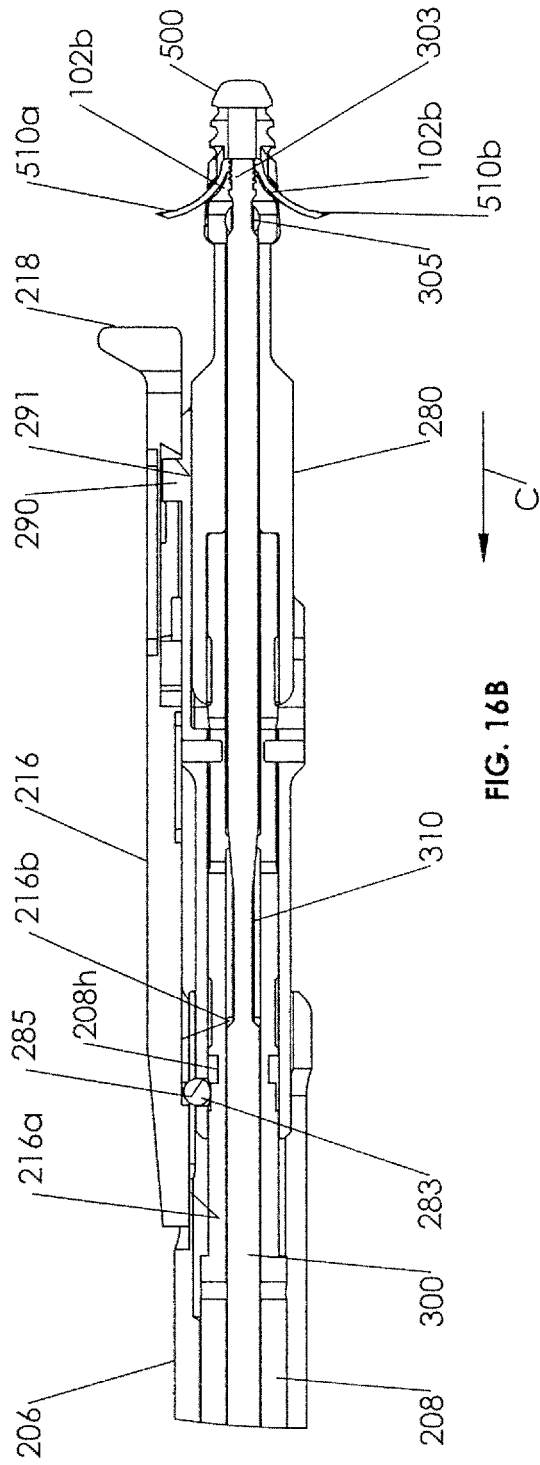
FIG. 16B is the view of FIG. 16A with the sliding cover moved proximally to a second position relative to inserter center shaft.
Figure 18:
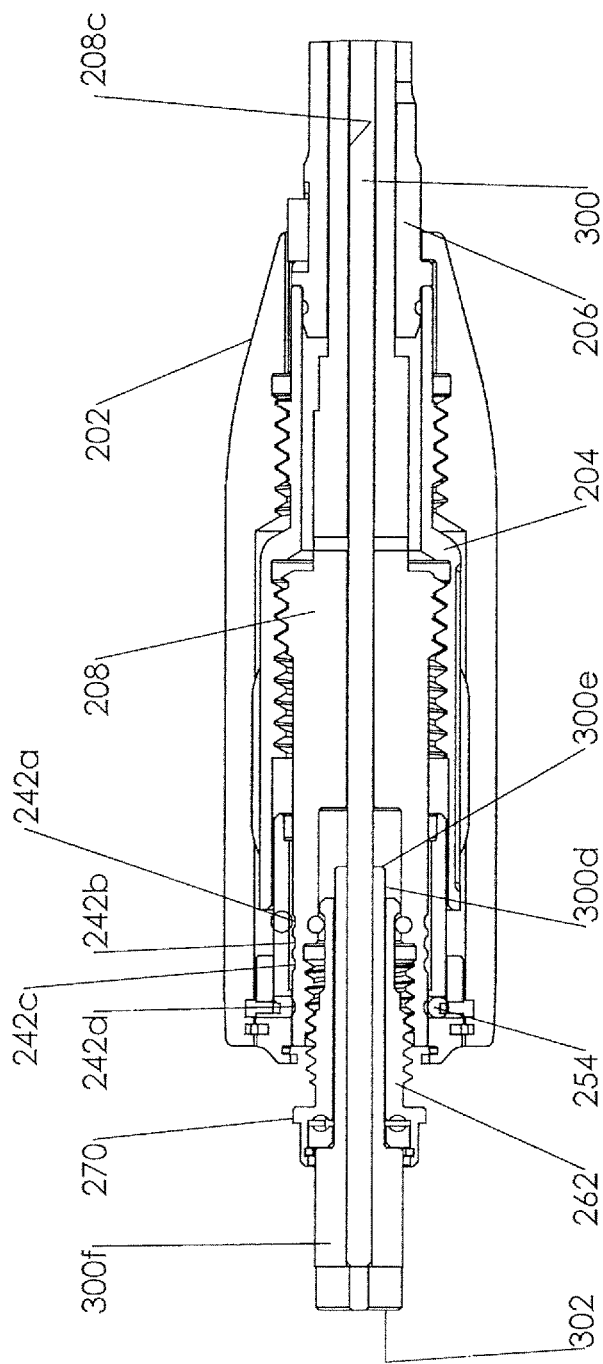
FIG. 18 is an enlarged sectional view of the proximal portion of the modular inserter assembly as shown in FIG. 8 with the depth stop moved to a position to facilitate release of the interbody fusion cage from the modular inserter assembly.
Figure 19A:
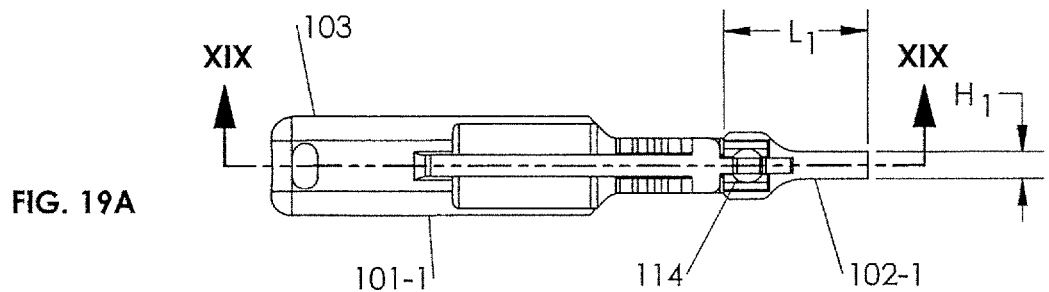
FIG. 19A is a side elevation view of a modular inserter tip for use with the modular inserter assembly of FIG. 1.
Figure 19B:
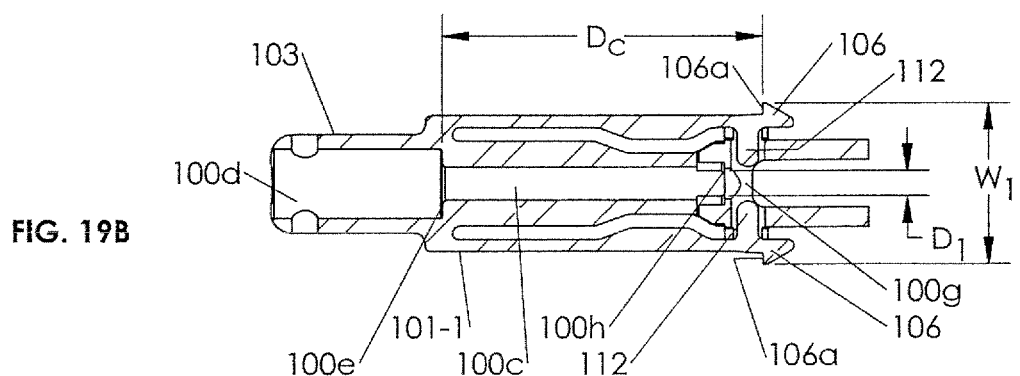
FIG. 19B is a cross-sectional view of the modular inserter tip as seen along viewing lines XIX-XIX of FIG. 19A
Figure 20A:
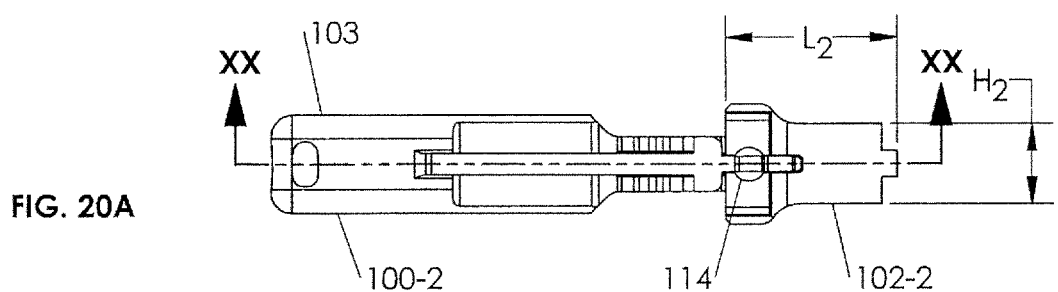
FIG. 20A is a side elevation view of a differently sized modular inserter tip for use with the modular inserter assembly of FIG. 1.
Figure 20B:
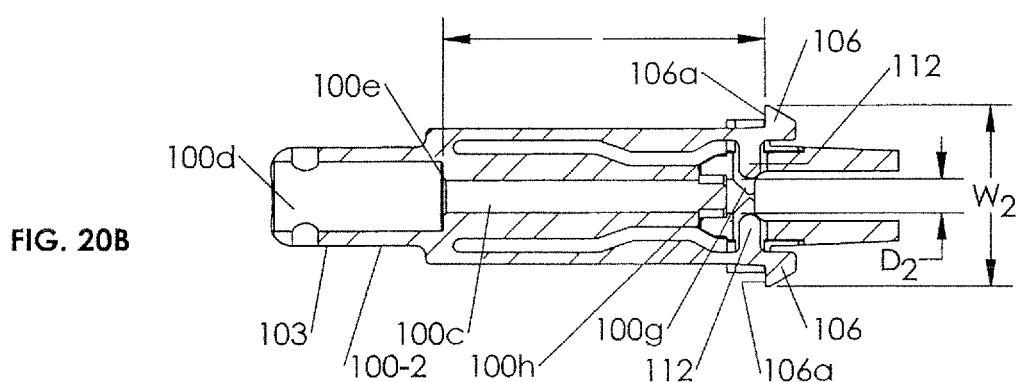
FIG. 20B is a cross-sectional view of the modular inserter tip as seen along viewing lines XX-XX of FIG. 20A

To prepare for separation of inserter assembly 10 from interbody fusion cage 500 after proper insertion of cage 500 into the intradiscal space and suitable deployment of anchor blades 510a, 510b, adjustment knob 204 is then rotated in a counterclockwise direction causing adjustment knob 204 and handle 202 to move axially proximally relative to center shaft 208. Rotation of adjustment knob 204 continues until ball bearings 254 enter the fourth set of proximal-most detent grooves 242d, as depicted in FIG. 18. The proximal movement of adjustment knob 254 also moves attached sleeve 206 with extension 216 thereon in the proximal direction. Extension 216 includes a boss 291 projecting downwardly from extension 216. During proximal movement of extension 216 boss 291 engages pad 290 projecting upwardly from sliding cover 280. At this stage, sliding cover 280 is in the first position relative to center shaft 208, as shown in FIG. 16a with ball bearing 283 disposed in notch 208h in center shaft 208. A lower surface 216a of extension 216 tangentially engages ball bearing 283 allowing depth stop 218 to move distally while keeping ball bearing within notch 208h and preventing ball bearing from moving radially. With ball bearing 283 maintained in position, depth stop 218 and extension 216 may move distally while sliding cover 280 is locked relative to center shaft 208. Further rotation of adjustment knob 204 causes sliding cover 280 to move proximally to the second position, as shown by arrow C in FIG. 16b. Sliding of sliding cover 280 is achievable as a result of pull rod radial relief 310 being aligned with second pair of prongs 294a, thereby allowing prongs 294a to move radially inwardly and separate from sliding cover slots 282b under the proximal axial force applied by boss 291 against pad 290 on sliding cover 280.

As sliding cover 280 is moved proximally, tines 288 at the distal end thereof, which are disposed in cavities 110 of modular inserter tip 100 in the first position as described hereinabove, are likewise moved proximally. Such proximal movement causes tines 288 to move out from cavities 110 and into contact with cams 108 on modular inserter tip flexible latches 104. Due to the flexibility of latches 104 relative to more rigid tines 288, engagement of tines 288 with cams 108 cause hooks 106 at the distal end of latches 104 to move radially inwardly to thereby move hooks 106 on modular inserter tip 100 out from slots 502 on interbody fusion cage 500. This allows separation of interbody fusion cage 500 from modular inserter tip 100 and thereby the modular inserter assembly 10. The surgeon will have an indication that such separation has occurred by tactile and audible feedback as a result of ball bearings 254 entering and engaging detent grooves 242d. During such proximal movement of extension 216 and sliding cover 280, lower surface 216a of extension 216 is moved out from contact with ball bearing 283 until undercut surface 216b is aligned with ball bearing 283, thereby allowing ball bearing 283 to move out from notch 208h in the proximal direction and allowing sliding cover to move axially relative to center shaft 208. Further motion of the sliding cover forces the ball out of notch 208h. At this stage, modular inserter assembly 10 is in position to be removed from the surgical site while the inserted interbody fusion cage 500 remains in place.

To effectuate separation of inserter assembly 10 from the inserted interbody fusion cage 500, pull rod 300 is unthreaded from anchor plate 510 but is not removed from depth stop 200, and T-handle 400 is removed. In this position, pull rod radial relief 310 remains aligned with second pair of prongs 294a and annular recess 305 remains aligned with modular inserter tip posts 112. The inserter assembly 10 may then be manually separated from inserted cage 500.

Upon removal of modular inserter assembly 10 from the surgical site, adjustment knob 204 is rotated clockwise causing depth stop 218 and extension 216 to move distally relative to center shaft 208 until bearings 254 are moved to into one of detent grooves 242a, 242b and 242c. During such movement ball bearing 282 is moved axially distally by engagement with extension lower surface 216a until ball bearing 283 is disposed in notch 208h, thereby moving the sliding cover 280 distally back to the first position relative to center shaft 208, as depicted in FIGS. 12 and 16a Pull rod 300 is then removed from inserter assembly 10 by manually pulling the pull rod 300 in a proximal direction. As a result, flexible prongs 292a are free to move in a radially inward direction toward lumen 208c, thereby allowing modular inserter tip 100 to be separated from center shaft 208 and pulled out from generally square internal pocket 286a of sliding cover 280 upon application of a manual pulling force. When a surgeon wishes to use the inserter assembly 10 for another procedure, a selected modular inserter tip 100 is attached to center shaft 208, as described above.

Having described the structure and function of modular inserter assembly 10 herein, it should be appreciated that a plurality of modular inserter tips 100 may be used with a single depth stop 200. In this regard, a kit of parts may be provided for use in spinal fusion surgery to insert an interbody fusion cage 500, selected from a group of differently sized cages 500, between a superior vertebra and an inferior vertebra. Such a kit may include a plurality of differently sized modular inserter tips 100 as shown in FIGS. 19A-B and 20A-B for use in conjunction with a selected interbody fusion cage 500. Such a kit may include, for example, a single depth stop 200, a T-handle 400, at least two modular inserter tips 100-1 and 100-2, two interbody fusion cages 500 each defining a different footprint, and two pull rods 300 of different sizes that are associated with a respectively different modular insert tip 100-1 and 100-2 and cage 500.

Each modular inserter tip 100-1 and 100-2 is substantially the same as modular inserter tip 100 described hereinabove, except as noted. As such, each modular inserter tip 100-1 and 100-2 is of generally parallelepiped configuration wherein the exterior surface 103 has a square cross-section of substantially the same size. As such, each modular inserter tip 100-1 and 100-2 may be received in generally square internal pocket 286a of sliding cover 280. Each modular inserter tip 100-1 and 100-2 also includes a counterbore 100d terminating in depth stop contact surface 100e for receipt of center shaft 208 of depth stop 200. As such, each modular inserter tip 100-1 and 100-2 may receive the distal end 208a of center shaft 208 with tip contact surface 208g contacting depth stop contact surface 100e. Similarly, the distance, $D_c$ between depth stop contact surface 100e and cage attachment surface 106a is substantially the same for each of modular inserter tips 100-1 and 100-2. This common distance, $D_c$ allows the depth stop indicator device 234 to provide a common readout of the depth that an interbody fusion cage 500 may be inserted since the cage attachment surface 106a is correlated with the cage proximal end 504.

The distal end of each modular inserter tip 100-1 and 100-2 differs in a manner to receive an interbody fusion cage 500 of different sizes. In this example, modular inserter tip 100-1 may be used with a smaller fusion cage 500, while modular inserter tip 100-2 may be used with a larger fusion cage 500. As such, modular inserter tip 100-1 may include a deployment ramp 102-1 having a distal height $H_1$ while modular inserter tip 100-2 be include deployment ramp 102-2 having a distal $H_2$ greater than $H_1$. In addition, the width, $W_1$ between hooks 106 in modular inserter tip 100-1 may be less than the width, $W_2$ between hooks 106 in modular inserter tip 100-2. Also, the length, $L_1$ of deployment ramp 102-1 may be less than $L_2$ of deployment ramp 102-2. While the diameter of central bore 100c of each modular inserter tip 100-1 and 100-2 is substantially the same, the diameter $D_1$ of rod pulling opening 100g in modular inserter tip 100-1 is less than the diameter $D_2$ of rod pulling opening 100g in modular inserter tip 100-2. Such differences in the diameters $D_1$ and $D_2$ allows for use of a modular inserter tip 100-1 or 100-2 with a mateable pull rod 300, thereby reducing the probability during surgery that blades of an anchor plate will not be properly deployed. In such exemplary use, modular inserter tip 100-1 may have the following dimensions: height $H_1$ of 4 mm, width $W_1$ of 12 ] mm, length $L_1$ of 10.7 mm. and an opening 100g diameter $D_1$ of 2.3 mm. Modular inserter tip 100-2 may have the following dimensions: height $H_2$ of 4 mm, width $W_2$ of 13.5 mm, length $L_2$ of 12.7 mm. and an opening 100g diameter $D_2$ of 2.5 mm.

In this example of a kit having at least two modular inserter tips 100-1 and 100-2, two differently sized interbody fusion cages 500 may also be provided in the kit. For example, a smaller interbody fusion cage 500 may have a width of 14 mm, a depth of 12 mm, and a maximum anatomic height of 8 mm, while the second larger interbody fusion cage may have a width of 15.5 mm, a depth of 14 mm and a maximum anatomic height of 8 mm. In addition, at least two pull rods 300 may be provided with each pull rod 300 having substantially the same construction as pull rod 300 described hereinabove but having different dimensions. In such exemplary use, a first smaller pull rod 300 for use with a smaller fusion cage 500 and smaller modular inserter tip 100-1, would have an overall length of 214 mm, a length $L_S$ of 28.2 mm, a length $L_R$ of 170.7 mm, an outer diameter of 2.2 mm for central shaft proximal portion 301a, and an outer diameter of 2.4 mm for central shaft distal portion 310b. A second larger pull rod 300 for use with a larger fusion cage 500 and larger modular inserter tip 100-2, would have an overall length of 214 mm, a length $L_S$ of 26.4 mm, a length $L_R$ of 172.5 mm, an outer diameter of 2.4 mm for central shaft proximal portion 301a, and an outer diameter of 2.4 mm for central shaft distal portion 310b.

As such, one particularly sized pull rod 300 may only be used with a particularly sized modular inserter tip 100-1 or 100-2 or interbody fusion cage 500. In this regard, if the larger pull rod 300 were to be inadvertently used with a smaller modular inserter tip 100-1, shoulder 306 of such larger rod would strike interior surface 100h and not pass through opening 100g having smaller diameter $D_1$, thereby preventing threaded extent 303 from threadably engaging threads 512 of anchor plate 510. In addition. In addition, if a smaller pull rod 300 were to be inappropriately chosen for use with a larger modular inserter tip 100-2, transverse surface 300e of such smaller rod would engage transverse surface 208e of inserter center shaft 208, thereby preventing threaded extent 303 from threadably engaging threads 512 of anchor plate 510. These conditions will indicate to the user that proper threading of the pull rod 300 to anchor plate 510 is not achieved and that a different pull rod 300 must be selected.

It should be understood that the examples provided herein are illustrative and that modular inserter tips 100, elongate pull rods 300 and interbody fusion cages 500 of other different sizes and dimensions may be used with the modular inserter assembly 10 described herein.

While the invention has been illustrated and described in detail in the drawings and foregoing description, it should be understood that such description is illustrative and not limiting. It should therefore be understood that various changes, modifications and further applications may be made without departing from the spirit of the invention and the scope of the appended claims.

What is claimed is:

1. A modular inserter assembly for use in inserting an interbody fusion cage between a superior vertebra and an inferior vertebra, the superior vertebra including an inferior endplate and a vertebral body, the inferior vertebra including a superior endplate and a vertebral body, the superior and inferior endplates defining a disc space therebetween, said modular inserter assembly comprising:
    a depth stop and a modular inserter tip releasably attached to said depth stop, said modular inserter tip including a cage attachment surface for releasable attachment to said interbody fusion cage, said depth stop including a movable stop axially movable relative to said inserter tip and being sized and configured to engage an exterior surface of one of said vertebrae when said interbody fusion cage is disposed in said disc space, said movable stop being spaced axially from a first location on said modular inserter tip by a selectively adjustable first distance, said modular inserter tip having a distal end and a proximal end, said distal end comprising a pair of flexible latches terminating in a pair of bilateral hooks for releasable attachment to said interbody fusion cage, said first location on said modular inserter tip is said cage attachment surface, each of said hooks comprising a cam cooperatively engageable with a movable portion of said depth stop to cause movement of said hooks toward each other in a manner to allow release from said interbody fusion device.

2. The modular inserter assembly of claim 1, wherein said depth stop comprises an indicator device operable with the movement of said depth stop to provide a visual indication of a plurality of selectable first distances, each first distance being denoted by a different indicator.

3. The modular inserter assembly of claim 2, wherein said indicator device provides an amplified indication of each of said different first distances.

4. The modular inserter assembly of claim 3, wherein each of said hooks includes a proximally facing surface defining said cage attachment surface.

5. The modular inserter assembly of claim 4, wherein the proximal end of said modular inserter tip includes a depth stop attachment surface.

6. The modular inserter assembly of claim 5, wherein said depth stop attachment surface comprises a pair of slots on opposite sides of said modular inserter tip.

7. The modular inserter assembly of claim 6, wherein said proximal end of said modular inserter tip includes an exterior surface having a generally square cross-section.

8. The modular inserter assembly of claim 7, wherein said proximal end of said modular inserter tip includes a counterbore extending therein in receipt of a portion of said depth stop, said counterbore terminating in an interior surface extending transversely within said modular inserter tip and defining a depth stop contact surface.

9. The modular inserter assembly of claim 8, wherein said distal end of said modular inserter tip includes an anchor deployment ramp projecting outwardly therefrom.

10. The modular inserter assembly of claim 9, wherein said anchor deployment ramp comprises opposite curvate surfaces to direct blades of an anchor plate disposed in said interbody fusion cage in substantially opposite directions.

11. A modular inserter assembly for use in inserting an interbody fusion cage between a superior vertebra and an inferior vertebra, the superior vertebra including an inferior endplate and a vertebral body, the inferior vertebra including a superior endplate and a vertebral body, the superior and inferior endplates defining a disc space therebetween, said modular inserter assembly comprising:
a depth stop and a modular inserter tip releasably attached to said depth stop,
said modular inserter assembly including a cage attachment surface for releasable attachment to said interbody fusion cage;
said depth stop including a movable stop axially movable relative to said modular inserter tip, said movable stop being sized and configured to engage an exterior surface of one of
said vertebrae when said interbody fusion cage is disposed in said disc space, said depth stop including a handle supporting an adjustment knob operable to axially move said movable stop to a plurality of selectable distances between the cage attachment surface and said movable stop, said adjustment knob being rotatable within said handle such that rotation of said adjustment knob axially moves said movable stop, said handle comprising an indicator device operable with the movement of said adjustment knob to provide an amplified visual indication of each of said plurality of selectable distances, said amplified visual indication being effected by first and second threaded connections within said depth stop handle, said depth stop comprising an elongate sleeve, said sleeve having a proximal end and a distal end, said proximal end being coupled to said adjustment knob for axial movement therewith and for rotational movement relative thereto, said movable stop being disposed adjacent the distal end of said sleeve.

12. The modular inserter assembly of claim 11, wherein said depth stop further comprises a generally cylindrical center shaft disposed within said handle, said center shaft having a proximal end and a distal end, said proximal end having markings thereon defining said indicator device, said center shaft comprising external threads thereon.

13. The modular inserter assembly of claim 12, wherein said adjustment knob is generally cylindrical having a proximal end and a distal end, wherein the distal end of said adjustment knob comprises external threads and said proximal end of said adjustment knob comprises internal threads.

14. The modular inserter assembly of claim 13, wherein said handle is generally cylindrical having a proximal end, a distal end and an interior surface within which said center shaft and said adjustment knob are disposed, said markings on said center shaft extending outwardly proximally from the proximal end of said handle, said interior surface of said handle comprising internal threads coupled with the external threads at the distal end of said adjustment knob to define said first threaded connection, and wherein said internal threads on said adjustment knob are coupled with the external threads on the distal end of said center shaft to define said second threaded connection.

15. The modular inserter assembly of claim 14, wherein rotation of said adjustment knob within said handle in a first rotational direction is operative via said first threaded connection to move said handle in an axial direction distally relative to said center shaft, thereby progressively exposing said markings of said indicator device outwardly proximally upon such rotational movement, and operative via said second threaded connection to move said adjustment knob and thereby said sleeve and said stop in the axial direction distally relative to said center shaft.

16. The modular inserter assembly of claim 15, wherein said first threaded connection is configured to move said handle in said axial direction distally relative to said center shaft in a first rate and wherein said second threaded connection is configured to move said adjustment knob and said stop relative to said center shaft in the axial direction in a second rate different from said first rate.

17. The modular inserter assembly of claim 16, wherein threads in said first threaded connection and said second threaded connection are provided with a pitch in opposite directions.

18. The modular inserter assembly of claim 17, wherein said pitch of said threads in said first threaded connection and said second threaded connection are substantially equal, resulting in said first rate being approximately twice the second rate.

19. The modular inserter assembly of claim 18, further including a tactile feedback element indicating incremental axial movement of said handle distally relative to said center shaft.

20. The modular inserter assembly of claim 19, wherein said tactile feedback element is defined by at least one spring loaded ball detent locatable in one of a series of grooves formed in said center shaft at predetermined axially spaced intervals adjacent the proximal end of said center shaft.

21. The modular inserter assembly of claim 20, wherein said at least one ball detent is supported by a bushing attached to said interior surface at the proximal end of said handle, a spring member applying a radial bias force to said at least one ball detent.

22. A modular inserter assembly for use in inserting an interbody fusion cage between a superior vertebra and an inferior vertebra, the superior vertebra including an inferior endplate and a vertebral body, the inferior vertebra including a superior endplate and a vertebral body, the superior and inferior endplates defining a disc space therebetween, said inserter assembly comprising:
a modular inserter tip including a cage attachment surface for releasable attachment to said interbody fusion cage of size and configuration for insertion into said disc space, said cage supporting an anchor plate having a deployable upper anchor blade and a deployable lower blade,
a depth stop releasably attached to said modular inserter tip and including a movable stop axially movable relative to said modular inserter tip, said movable stop being sized and configured to engage an exterior surface of one of said vertebrae when said interbody fusion cage is disposed in said disc space, said depth stop including a handle supporting an adjustment knob operable to axially move said movable stop to a plurality of selectable distances between the cage attachment surface and said movable stop, said adjustment knob being rotatable within said handle such that rotation of said adjustment knob axially moves said movable stop, said depth stop including an indicator device operable with the movement of said adjustment knob to provide a visual indication of each of said plurality of selectable distances, said depth stop including a movable locking element movably attached to said depth stop and releasably attached to said modular inserter tip, said depth stop comprising an elongate sleeve, said sleeve having a proximal end and a distal end, said proximal end being coupled to said adjustment knob for axial movement therewith and for rotational movement relative thereto, said movable stop being disposed adjacent the distal end of said sleeve, and said depth stop further including an elongate pull rod extending within said handle, said pull rod having a distal end for extending into said cage and for releasably attaching to said anchor plate, said pull rod being operable to move proximally relative to said modular inserter tip to deploy said upper anchor blade and said lower anchor blade.

23. The modular inserter assembly of claim 22, wherein depth stop further comprises a generally cylindrical center shaft disposed within said handle, said center shaft having a proximal end and a distal end, said center shaft having a lumen extending therethrough, said elongate pull rod being movably received in said lumen.

24. The modular inserter assembly of claim 23, wherein rotation of said adjustment knob within said handle is operative to move said adjustment knob and thereby said sleeve with said stop thereon axially relative to said center shaft.

25. The modular inserter assembly of claim 24 wherein said center shaft is releasably attached to said modular inserter tip by said movable locking element.

26. The modular inserter assembly of claim 25, wherein said movable locking element comprises a sliding cover slidable on the distal end of said center shaft from a first position to a second position.

27. The modular inserter assembly of claim 26 wherein said center shaft comprises at its distal end a first pair and a second pair of bilateral flexible locking prongs axially spaced from each other, said first pair of flexible prongs being releasably attached to said modular inserter tip and said second pair of flexible prongs being releasably attached to said sliding cover.

28. The modular inserter assembly of claim 27 wherein with said sliding cover being in said first position, said elongate pull rod has a surface portion in engagement with said first pair and said second pair of flexible prongs in a manner to prevent flexing movement thereof, thereby locking said sliding cover relative to said center shaft and preventing axial movement therebetween and locking said sliding cover to said modular inserter tip and preventing separation of said modular inserter tip from said sliding cover.

29. The modular inserter assembly of claim 28 wherein said elongate pull rod comprises a radial relief, said radial relief being disposed between said first pair and said second pair of flexible prongs when said sliding cover is in said first position.

30. The modular inserter assembly of claim 29 wherein said elongate pull rod is movable proximally in a manner to axially move said radial relief to be in alignment with said second pair of flexible prongs that are releasably attached to said sliding cover, thereby allowing sufficient flexing of said second pair of flexible prongs to unlock the attachment between said sliding cover and said center shaft while maintaining the lock between said sliding cover and said modular inserter tip.

31. The modular inserter assembly of claim 30, wherein said sleeve comprises an extension including a boss projecting toward said sliding cover, and wherein said sliding cover includes a pad projecting toward said sleeve extension, and wherein upon rotation of said adjustable knob said sleeve with said boss is moved proximally causing engagement of said boss with said pad on said locking cover, thereby causing proximal movement of said sliding cover to said second position.

32. The modular inserter assembly of claim 31 wherein said modular inserter tip comprises a pair of flexible latches terminating in a pair of bilateral hooks for releasable attachment to said interbody fusion cage, and wherein upon movement of said sliding cover to said second position said sliding cover causes movement of said flexible latches in a manner to separate said modular inserter tip from said interbody fusion cage.

33. The modular inserter assembly of claim 32, wherein said center shaft has internal threads at the proximal end thereof, and wherein said inserter assembly further comprises a deployment screw having external threads in threaded engagement with said internal threads of said center shaft.

34. The modular inserter assembly of claim 33 wherein said elongate pull rod comprises an elongate shaft including a head at the proximal end of said shaft, a distal end of said head defining an engagement surface configured to cooperate with said deployment screw, wherein upon rotation of said deployment screw within said center shaft said deployment screw moves axially in the proximal direction and imparts an axial force to said engagement surface in a manner to move said elongate pull rod in the proximal direction relative to said center shaft.

35. The modular inserter assembly of claim 34, wherein proximal movement of said elongate pull rod a first distance causes deployment of said upper anchor blade and said lower anchor blade.

36. The modular inserter assembly of claim 35 wherein proximal movement of said elongate pull rod to a second distance causes movement of said sliding cover to said second position in a manner to separate said modular inserter tip from said interbody fusion cage.

37. The modular inserter assembly of claim 33, wherein said deployment screw comprises a drive surface, and wherein said inserter assembly further includes an actuator cooperating with said drive surface to rotate said deployment screw.

* * * * *